(12) United States Patent
Fadli

(10) Patent No.: US 10,245,223 B2
(45) Date of Patent: Apr. 2, 2019

(54) USE FOR DYEING KERATIN FIBRES OF A COMPOUND OF AZOMETHINE TYPE BEARING A PYRAZOLOPYRIDINE UNIT

(71) Applicant: L'OREAL, Paris (FR)

(72) Inventor: Aziz Fadli, Chelles (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 15/536,739

(22) PCT Filed: Dec. 17, 2015

(86) PCT No.: PCT/EP2015/080321
§ 371 (c)(1),
(2) Date: Jun. 16, 2017

(87) PCT Pub. No.: WO2016/097196
PCT Pub. Date: Jun. 23, 2016

(65) Prior Publication Data
US 2017/0348215 A1    Dec. 7, 2017

(30) Foreign Application Priority Data

Dec. 19, 2014   (FR) ...................................... 14 63004

(51) Int. Cl.
| A61Q 5/10 | (2006.01) |
| A61K 8/49 | (2006.01) |
| C07D 471/04 | (2006.01) |
| A61K 8/22 | (2006.01) |
| A61Q 5/06 | (2006.01) |

(52) U.S. Cl.
CPC ................ *A61K 8/492* (2013.01); *A61K 8/22* (2013.01); *A61Q 5/065* (2013.01); *C07D 471/04* (2013.01)

(58) Field of Classification Search
CPC .......... A61Q 5/10; A61Q 5/065; A61K 8/492; C07D 471/04
See application file for complete search history.

(56) References Cited

U.S. PATENT DOCUMENTS

| 4,003,699 A | 1/1977 | Rose et al. |
| RE30,199 E | 1/1980 | Rose et al. |
| 5,061,289 A | 10/1991 | Clausen et al. |
| 5,380,340 A | 1/1995 | Neunhoeffer et al. |
| 5,534,267 A | 7/1996 | Neunhoeffer et al. |
| 5,663,366 A | 9/1997 | Neunhoeffer et al. |
| 5,708,151 A | 1/1998 | Möckli |
| 5,766,576 A | 6/1998 | Löwe et al. |
| 5,792,221 A | 8/1998 | Lagrange et al. |
| 6,099,592 A | 8/2000 | Vidal et al. |
| 6,099,593 A | 8/2000 | Terranova et al. |
| 6,284,003 B1 | 9/2001 | Rose et al. |
| 6,338,741 B1 | 1/2002 | Vidal et al. |
| 6,645,258 B2 | 11/2003 | Vidal et al. |
| 6,884,265 B2 | 4/2005 | Vidal et al. |
| 7,060,110 B2 | 6/2006 | Vidal et al. |
| 7,582,123 B2 | 9/2009 | Fadli et al. |
| 7,887,601 B2 * | 2/2011 | Fadli ...................... A61K 8/494 548/367.7 |
| 2002/0053111 A1 | 5/2002 | Kravtchenko et al. |
| 2003/0019049 A9 | 1/2003 | Kravtchenko et al. |

(Continued)

FOREIGN PATENT DOCUMENTS

| DE | 2359399 A1 | 6/1975 |
| DE | 3843892 A1 | 6/1990 |

(Continued)

OTHER PUBLICATIONS

STIC Search Report dated Jul. 2, 2018.*
International Search Report for PCT/EP2016/080321, dated Feb. 22, 2016.

*Primary Examiner* — Eisa B Elhilo
(74) *Attorney, Agent, or Firm* — The Marbury Law Group, PLLC

(57) ABSTRACT

The invention relates to a compound chosen from dyes of azomethine type bearing a pyrazolopyridine unit of formula (I) and the leuco forms thereof of formula (II) below, and also the optical isomers and geometrical isomers thereof, the tautomers thereof, the addition salts thereof with an acid or a base, and the solvates thereof. The invention also relates to the use of these particular compounds for dyeing keratin fibers.

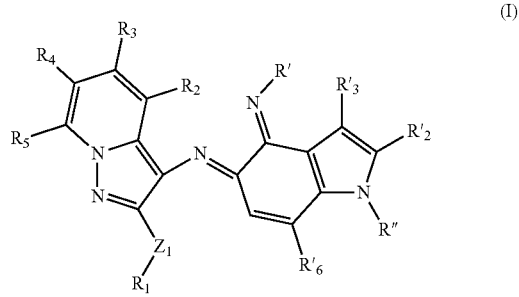

(I)

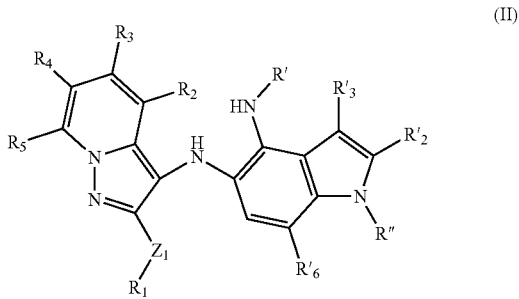

(II)

14 Claims, No Drawings

(56) References Cited

U.S. PATENT DOCUMENTS

| | | |
|---|---|---|
| 2003/0106169 A1 | 6/2003 | Vidal et al. |
| 2004/0093675 A1 | 5/2004 | Vidal et al. |
| 2004/0093676 A1 | 5/2004 | Vidal et al. |
| 2004/0107513 A1 | 6/2004 | Vidal et al. |
| 2004/0127692 A1 | 7/2004 | David et al. |
| 2004/0143911 A1 | 7/2004 | Vidal |
| 2004/0168263 A1 | 9/2004 | Vidal |
| 2004/0200009 A1 | 10/2004 | Vidal |
| 2004/0244123 A1 | 12/2004 | Vidal et al. |
| 2005/0039268 A1 | 2/2005 | Plos et al. |
| 2007/0136959 A1 | 6/2007 | Fadli |
| 2007/0143935 A1 | 6/2007 | Fadli et al. |
| 2009/0044348 A1 | 2/2009 | Fadli et al. |
| 2010/0115711 A1 | 5/2010 | Fadli et al. |

FOREIGN PATENT DOCUMENTS

| | | |
|---|---|---|
| DE | 4133957 A1 | 4/1993 |
| DE | 19543988 A1 | 5/1997 |
| EP | 0714954 A2 | 6/1996 |
| EP | 0770375 A1 | 5/1997 |
| EP | 1792606 A1 | 6/2007 |
| EP | 1792903 A1 | 6/2007 |
| EP | 2011787 A1 | 1/2009 |
| FR | 2692572 A1 | 12/1993 |
| FR | 2733749 A1 | 11/1996 |
| FR | 2750048 A1 | 12/1997 |
| FR | 2807652 A1 | 10/2001 |
| FR | 2822693 A1 | 10/2002 |
| FR | 2822694 A1 | 10/2002 |
| FR | 2822696 A1 | 10/2002 |
| FR | 2822698 A1 | 10/2002 |
| FR | 2825625 A1 | 12/2002 |
| FR | 2825702 A1 | 12/2002 |
| FR | 2829926 A1 | 3/2003 |
| FR | 2844269 A1 | 3/2004 |
| FR | 2917737 A1 | 12/2008 |
| FR | 2999422 A1 | 6/2014 |
| GB | 1026978 A | 4/1966 |
| GB | 1153196 A | 5/1969 |
| JP | 02-019576 A | 1/1990 |
| JP | 05-163124 A | 6/1993 |
| WO | 94/08969 A1 | 4/1994 |
| WO | 94/08970 A1 | 4/1994 |
| WO | 95/01772 A1 | 1/1995 |
| WO | 95/15144 A1 | 6/1995 |
| WO | 96/15765 A1 | 5/1996 |
| WO | 02/078660 A1 | 10/2002 |
| WO | 02/100369 A2 | 12/2002 |
| WO | 02/100834 A1 | 12/2002 |

\* cited by examiner

USE FOR DYEING KERATIN FIBRES OF A COMPOUND OF AZOMETHINE TYPE BEARING A PYRAZOLOPYRIDINE UNIT

CROSS REFERENCE TO RELATED APPLICATIONS

This is a national stage application of PCT/EP2015/080321, filed internationally on Dec. 17, 2015, which claims priority to French Application No. 1463004, filed on Dec. 19, 2014, both of which are incorporated by reference herein in their entireties.

The present invention relates to novel compounds of azomethine type bearing a pyrazolopyridine unit and to the use thereof for dyeing keratin fibres, and in particular human keratin fibres such as the hair.

It is known practice to dye keratin fibres with dye compositions containing direct dyes. These compounds are coloured and colouring molecules that have an affinity for the fibres. It is known practice, for example, to use direct dyes of the nitrobenzene type, anthraquinone or nitropyridine dyes, and dyes of the azo, xanthene, acridine, azine or triarylmethane type.

These dyes are usually applied to keratin fibres optionally in the presence of an oxidizing agent if it is desired to obtain simultaneous lightening of the fibres. Once the leave-on time has elapsed, the fibres are rinsed, optionally washed and dried.

The colourings resulting from the use of direct dyes are colourings that are often chromatic but are, however, only temporary or semi-permanent since the nature of the interactions that bind the direct dyes to the keratin fibre and their desorption from the surface and/or the core of the fibre are responsible for their weak dyeing power and their poor relative persistence with respect to washing or perspiration. These direct dyes are also generally light-sensitive since the resistance of the chromophore to photochemical attack is low, leading to fading of the colouring of the hair over time. The sensitivity of these dyes to light depends on their uniform distribution or their distribution as aggregates in and/or on the keratin fibre.

To obtain the same result, it is also possible to use the uncoloured reduced form of these dyes and to apply it to the keratin fibres in the presence of an oxidizing agent in order to generate the coloured and colouring oxidized form. The colouring obtained may then be faded out and then reformed rapidly by changing from one form to the other.

Thus, it is known from French patent application No. 2 917 737 to use compounds of azomethine type bearing a pyrazolinone unit and the reduced forms thereof to obtain a colouring on keratin fibres that can be faded out and then reformed readily.

The aim of the present invention is to provide novel direct dyes for reversibly dyeing keratin fibres while at the same time leading to good dyeing properties.

In particular, one of the aims of the present invention is to provide direct dyes that make it possible to obtain a strong, chromatic, aesthetic, sparingly selective colouring with varied shades, which shows good resistance to the various attacking factors to which the hair may be subjected such as shampoos, light, sweat and permanent reshaping, and which can be faded out easily.

The Applicant has thus discovered, surprisingly, that particular compounds chosen from dyes of azomethine type bearing a pyrazolopyridine unit of formula (I) as defined below, and the leuco forms thereof (II), and also the optical and geometrical isomer forms and tautomers thereof, the addition salts thereof with an acid or a base and the solvates thereof such as hydrates make it possible to achieve this aim.

One subject of the invention is thus a compound chosen from dyes of azomethine type bearing a pyrazolopyridine unit of formula (I) and the leuco forms thereof of formula (II) below, and also the optical isomers and geometrical isomers thereof, the tautomers thereof, the addition salts thereof with an acid or a base, and the solvates thereof such as hydrates:

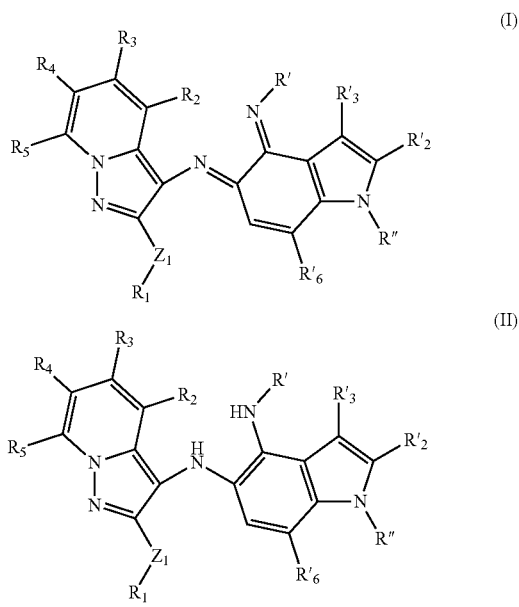

in which formulae (I) and (II):

$Z_1$ represents an oxygen atom or a group —N($R_6$)—;

when $Z_1$ represents —N($R_6$)—, then $R_1$ and $R_6$ may form, together with the nitrogen atom to which they are attached, an optionally substituted, optionally cationic, 5- to 8-membered, saturated, unsaturated or aromatic heterocycle;

$R_1$ and $R_6$ each independently represent:
a hydrogen atom;
a $C_1$-$C_{10}$ alkyl radical optionally interrupted with one or more non-adjacent heteroatoms, preferably oxygen, and/or optionally substituted, preferably with one or more groups chosen from i) hydroxyl, ii) optionally substituted 5- to 8-membered, saturated, unsaturated or aromatic (hetero)cycle, iii) —N(R')R'', iv) —N$^+$R'R''R''' with R', R'' and R''' each independently representing a $C_1$-$C_6$ alkyl group;
an optionally substituted, saturated, unsaturated or aromatic 5- to 8-membered (hetero)cycle;
in particular, $R_1$ represents a (poly)hydroxy($C_1$-$C_6$ alkyl), preferably hydroxy($C_1$-$C_6$ alkyl) group and $Z_1$ represents an oxygen atom;

$R_2$, $R_3$, $R_4$ and $R_5$ each independently represent:
a hydrogen atom;
an optionally substituted $C_1$-$C_4$ alkyl radical,
a group chosen from —NH$_2$, —N(H)—$R_{10}$, —N($R_{11}$)—$R_{12}$, OH and —OR$_9$, with $R_9$ and $R_{10}$ representing an optionally substituted, linear or branched $C_1$-$C_6$ alkyl, $R_{11}$ and $R_{12}$, which may be identical or different, representing an optionally substituted, linear or branched $C_1$-$C_6$ alkyl, it being possible for $R_{11}$ and $R_{12}$ to form, together with the nitrogen atom to which they are attached, a saturated, unsaturated or aromatic 5- to 8-membered heterocycle optionally containing one or more other heteroatoms or groups chosen from oxygen and nitrogen, the heterocycle being optionally substituted;

$R_2$, $R_3$, $R_4$ and $R_5$ may form, in pairs, with adjacent radicals, an optionally substituted, saturated or unsaturated or aromatic (hetero)cycle;

$R'_2$ and $R'_3$, which may be identical or different, represent:
   a hydrogen atom;
   a $C_1$-$C_6$ and preferably $C_1$-$C_4$ alkyl radical, optionally substituted with one or more hydroxyl radicals;
   a $C_1$-$C_6$ alkyl carboxylate radical;
   a carboxyl radical;

$R'$ represents:
   a hydrogen atom;
   a $C_1$-$C_6$ alkyl radical;

$R'_6$ represents:
   a hydrogen atom;
   a halogen atom;
   a linear or branched $C_1$-$C_{10}$ alkyl radical, optionally interrupted with one or more non-adjacent oxygen atoms and/or one or more non-adjacent divalent groups —N($R'_9$)— and optionally substituted with one or more radicals, which may be identical or different, chosen from —OH and —N($R'_7$)$R'_8$;
   a carboxyl radical;
   a $C_1$-$C_{10}$ alkyl carboxylate;
   a radical —CONR$'_7$R$'_8$;
   a $C_1$-$C_{10}$ alkoxy radical or a $C_1$-$C_{10}$ (poly)hydroxyalkoxy radical;
   a (poly)($C_1$-$C_{10}$ alkoxy)-($C_1$-$C_{10}$ alkoxy) radical;
   a radical —O-Ak-N($R'_9$)$R'_{10}$ in which Ak is a linear $C_1$-$C_8$ or branched $C_3$-$C_8$ divalent alkylene radical, optionally interrupted with one or more oxygen atoms and/or non-adjacent divalent groups —N($R'_7$)—;

$R'_7$ and $R'_8$, which may be identical or different, represent:
   a hydrogen atom;
   a $C_1$-$C_8$ alkyl radical optionally substituted with one or more hydroxyl radicals;

$R'_9$ and $R'_{10}$, which may be identical or different, represent i) a linear or branched $C_1$-$C_6$ alkyl radical, ii) a $C_2$-$C_6$ alkenyl radical or iii) a $C_2$-$C_6$ alkynyl radical;

$R'_9$ and $R'_{10}$ may form, with the nitrogen that bears them, a saturated or unsaturated 5- to 8-membered heterocycle, one of the chain members possibly being an oxygen atom or a nitrogen atom, or a divalent radical —N($R'_{11}$)— with $R'_{11}$ representing a hydrogen atom or a $C_1$-$C_4$ alkyl group, optionally substituted with one or more radicals chosen from —OH, —N($R'_7$)$R'_8$ and $C_1$-$C_4$ alkyl;

R" represents:
   a hydrogen atom;
   a linear or branched $C_1$-$C_{10}$ alkyl radical, optionally interrupted with an oxygen atom or a divalent group —N(R)— with R representing a hydrogen atom or a $C_1$-$C_4$ alkyl group;

it being understood that when the compound of formula (I) or (II) is positively charged, then it comprises as many anionic counterions as cationic charges to achieve the electrical neutrality of the molecule.

The compounds according to the invention, as defined above, are useful for dyeing keratin fibres. They make it possible to obtain a strong, chromatic, aesthetic, sparingly selective colouring in varied shades, which can be faded out easily and/or which can be recoloured easily after fading out. In addition, the colourings obtained using dye (I) or (II) withstand the various attacking factors to which hair may be subjected, such as shampooing, light, sweat and permanent reshaping.

A subject of the present invention is also the use for dyeing keratin fibres of one or more compounds according to the invention.

More particularly, they lead to intense colourings at different pH values, better still at neutral and basic pH, and even more preferentially at neutral pH.

Another subject is a composition for dyeing keratin fibres, comprising, in a medium that is suitable for dyeing keratin fibres, one or more compounds according to the invention.

A subject of the present invention is also a process for dyeing keratin fibres using one or more compounds according to the invention.

A subject of the present invention is also a multi-compartment device for performing the process in accordance with the invention.

Other subjects, characteristics, aspects and advantages of the invention will emerge even more clearly on reading the description and the examples that follow.

In the text hereinbelow, unless otherwise indicated, the limits of a range of values are included in that range, especially in the expressions "between" and "ranging from . . . to . . . ".

The expression "at least one" used in the present description is equivalent to the expression "one or more".

In the context of the invention, unless otherwise mentioned, the term "alkyl radical" means linear or branched alkyl radicals.

The saturated or unsaturated and optionally fused rings can also be optionally substituted.

The alkyl radicals are saturated, linear or branched hydrocarbon-based radicals, generally of $C_1$-$C_{10}$ and preferably $C_1$-$C_6$, such as methyl, ethyl, propyl, butyl, pentyl and hexyl.

The alkenyl radicals are unsaturated, linear or branched $C_2$-$C_{10}$ hydrocarbon-based radicals, comprising at least one double bond, particularly $C_2$-$C_6$ alkenyl radicals such as ethylene, propylene, butylene, pentylene, 2-methylpropylene and decylene.

The alkynyl radicals are unsaturated, linear or branched $C_2$-$C_{10}$ hydrocarbon-based radicals, comprising at least one triple bond, particularly $C_2$-$C_6$ alkynyl radicals.

The alkoxy radicals are alkyl-oxy radicals with alkyl as defined above, preferably $C_1$-$C_{10}$ alkyl, such as methoxy, ethoxy, propoxy and butoxy.

The alkoxyalkyl radicals are preferably ($C_1$-$C_{20}$)alkoxy ($C_1$-$C_{20}$)alkyl radicals, such as methoxymethyl, ethoxymethyl, methoxyethyl and ethoxyethyl.

For the purposes of the present invention, the term "interrupted" means that the alkyl group is interrupted on the carbon-based chain of said alkyl with one or more heteroatoms. Examples that may be mentioned include -Ak-O-Ak", -Ak-N(R)-Ak", -Ak-O-Ak'-N(R)-Ak", -Ak-N(R)-Ak'-N(R)-Ak" or -Ak-O-Ak'-O-Ak", with Ak and Ak' representing $C_1$-$C_4$ alkylene groups and Ak" representing a $C_1$-$C_4$ alkyl group.

The halogen atoms are fluorine, chlorine, bromine and iodine atoms.

The "alkylcarbonyl" radicals are alkyl-carbonyl radicals with alkyl as defined previously, preferably $C_1$-$C_{10}$ alkyl, such as acetyl or propionyl.

The "alkoxycarbonyl" radicals are —O—C(O)-alkyl radicals with alkyl as defined previously, for instance acetate, propionate, citrate, tartrate, gluconate and lactate.

The "alkyl", "alkenyl", "cyclic" or "cycloalkyl" radicals, when they are substituted, are substituted with at least one substituent borne by at least one carbon atom chosen from: 1) a halogen atom, a group chosen from 2) hydroxyl; 3) oxo; 4) $C_1$-$C_2$ alkoxy; 5) $C_1$-$C_{10}$ alkoxycarbonyl; 6) $C_1$-$C_{10}$ alkylcarbonyl; 7) (poly)hydroxy($C_2$-$C_4$)alkyl; 8) (poly)hydroxy($C_2$-$C_4$)alkoxy; 9) amino; 10) quaternary ammonium —$N^+R'R''R'''$, $M^-$ for which R', R" and R'", which may be identical or different, represent a hydrogen atom, or a $C_1$-$C_4$ alkyl group; and $M^-$ represents an anionic counterion, preferably a halide; 11) 5- or 6-membered heterocycloalkyl; 12) optionally cationic 5- or 6-membered heteroaryl, preferably imidazolium, optionally substituted with a $C_1$-$C_4$ alkyl radical, preferentially methyl; 13) amino substituted with one or two identical or different $C_1$-$C_6$ alkyl radicals optionally bearing at least: i) a hydroxyl group, ii) amino optionally substituted with one or two $C_1$-$C_3$ alkyl radicals, it being possible for said alkyl radicals to form, with the nitrogen atom to which they are attached, a saturated or unsaturated 5- to 7-membered heterocycle optionally comprising at least one other nitrogen or non-nitrogen heteroatom, iii) quaternary ammonium —$N^+R'R''R'''$, $M^-$ for which R', R" and R'", which may be identical or different, represent a hydrogen atom or a $C_1$-$C_4$ alkyl group; and $M^-$ represents an anionic counterion, preferably a halide, iv) optionally cationic 5- or 6-membered heteroaryl, preferentially imidazolium, optionally substituted with a $C_1$-$C_4$ alkyl radical, preferentially methyl; 14) acylamino (—NR—C(O)—R') in which the radical R is a hydrogen atom or a $C_1$-$C_4$ alkyl radical optionally bearing at least one hydroxyl group and the radical R' is a $C_1$-$C_2$ alkyl radical; 15) carbamoyl ((R)$_2$N—C(O)—) in which the radicals R, which may be identical or different, represent a hydrogen atom or a $C_1$-$C_4$ alkyl radical optionally bearing at least one hydroxyl group; 16) alkylsulfonylamino (R'S(O)$_2$—N(R)—) in which the radical R represents a hydrogen atom or a $C_1$-$C_4$ alkyl radical optionally bearing at least one hydroxyl group and the radical R' represents a $C_1$-$C_4$ alkyl radical, a phenyl radical; 17) aminosulfonyl ((R)$_2$N—S(O)$_2$—) in which the radicals R, which may be identical or different, represent a hydrogen atom or a $C_1$-$C_4$ alkyl radical optionally bearing at least one hydroxyl group; 18) carboxyl in acid or salified form (preferably salified with an alkali metal or a substituted or unsubstituted ammonium); 19) cyano; 20) nitro; 21) nitroso; 22) phenoxy optionally substituted with one or more hydroxyl groups; 23) phenylcarbonyloxy optionally substituted with one or more hydroxyl groups; 24) phenyloxycarbonyl optionally substituted with one or more hydroxyl groups; and 25) a phenyl group optionally substituted with one or more hydroxyl groups.

The "aryl", "heterocyclic" or "heteroaryl" radicals or the aryl, heteroaryl or heterocyclic part of the radicals, when they are substituted, are substituted with at least one substituent borne by at least one carbon atom, chosen from: 1) halogen; 2) $C_1$-$C_{10}$ alkyl, preferably $C_1$-$C_8$ alkyl, optionally substituted with one or more radicals chosen from the following radicals: i) hydroxyl, ii) $C_1$-$C_2$ alkoxy, iii) (poly)hydroxy($C_2$-$C_4$)alkoxy, iv) acylamino, v) amino substituted with two identical or different $C_1$-$C_4$ alkyl radicals optionally bearing at least one hydroxyl group or it being possible for the two radicals to form, with the nitrogen atom to which they are attached, a saturated or unsaturated 5- to 7-membered, preferably 5- or 6-membered, heterocycle optionally comprising another nitrogen or non-nitrogen heteroatom; 3) hydroxyl; 4) $C_1$-$C_2$ alkoxy; 5) $C_1$-$C_{10}$ alkoxycarbonyl; 6) $C_1$-$C_{10}$ alkylcarbonyloxy; 7) (poly)hydroxy($C_2$-$C_4$)alkoxy; 8) amino; 9) 5- or 6-membered heterocycloalkyl; 10) optionally cationic 5- or 6-membered heteroaryl, preferably imidazolium, optionally substituted with a ($C_1$-$C_4$)alkyl radical, preferentially methyl; 11) amino substituted with one or two identical or different $C_1$-$C_6$ alkyl radicals optionally bearing at least: i) hydroxyl, ii) amino optionally substituted with one or two $C_1$-$C_3$ alkyl radicals, it being possible for said alkyl radicals to form, with the nitrogen atom to which they are attached, a saturated or unsaturated 5- to 7-membered heterocycle optionally comprising at least one other nitrogen or non-nitrogen heteroatom, iii) quaternary ammonium —$N^+R'R''R'''$, $M^-$ for which R', R" and R'", which may be identical or different, represent a hydrogen atom or a $C_1$-$C_4$ alkyl group; and $M^-$ represents an anionic counterion, preferably a halide, iv) optionally cationic 5- or 6-membered heteroaryl, preferentially imidazolium, optionally substituted with a $C_1$-$C_4$ alkyl radical, preferentially methyl; 12) quaternary ammonium —$N^+R'R''R'''$, $M^-$ for which R', R", R'" and $M^-$ are as defined previously; 13) acylamino (—N(R)—C(O)—R') in which the radical R is a hydrogen atom or a $C_1$-$C_4$ alkyl radical optionally bearing at least one hydroxyl group and the radical R' is a $C_1$-$C_2$ alkyl radical; 14) carbamoyl ((R)$_2$N—C(O)—) in which the radicals R, which may be identical or different, represent a hydrogen atom or a $C_1$-$C_4$ alkyl radical optionally bearing at least one hydroxyl group; 15) alkylsulfonylamino (R'S(O)$_2$—N(R)—) in which the radical R represents a hydrogen atom or a $C_1$-$C_4$ alkyl radical optionally bearing at least one hydroxyl group and the radical R' represents a $C_1$-$C_4$ alkyl radical, a phenyl radical; 16) aminosulfonyl ((R)$_2$N—S(O)$_2$—) in which the radicals R, which may be identical or different, represent a hydrogen atom or a $C_1$-$C_4$ alkyl radical optionally bearing at least one hydroxyl group; 17) carboxyl in acid or salified form (preferably salified with an alkali metal or a substituted or unsubstituted ammonium); 18) cyano; 19) nitro; 20) nitroso; 21) polyhaloalkyl, preferentially trifluoromethyl; 22) carboxyl; 23) phenylcarbonyloxy optionally substituted with one or more hydroxyl groups; 24) phenyloxycarbonyl optionally substituted with one or more hydroxyl groups; 25) phenyl optionally substituted with one or more hydroxyl or alkoxy groups; and 26) phenoxy.

The term "optionally substituted amino" means an amino group which may bear one or two 1) identical or different $C_1$-$C_6$ alkyl radicals optionally bearing at least: i) a hydroxyl group, ii) an amino group optionally substituted with one or two $C_1$-$C_3$ alkyl radicals, said alkyl radicals or the two alkyl radicals form, with the nitrogen atom to which they are attached, a saturated or unsaturated, optionally substituted 5- to 7-membered heterocycle optionally comprising at least one other nitrogen or non-nitrogen heteroatom; 2) —C(O)(alkyl), the alkyl group possibly being substituted; 3) —C(O)O(alkyl), the alkyl group possibly being substituted; 4) —C(O)NH(alkyl), the alkyl group possibly being substituted; 5) —SO$_2$(alkyl), the alkyl group possibly being substituted.

The "cyclic" radicals are fused or non-fused, saturated or unsaturated, aromatic or non-aromatic monocyclic or polycyclic radicals, comprising from 4 to 30 carbon ring members, preferentially from 5 to 15 carbon atoms, optionally substituted with one or more atoms or groups as defined previously, especially one or more alkyl, alkoxy, carboxyl, hydroxyl, amine or oxo groups.

The "aryl" radicals are fused or non-fused, monocyclic or polycyclic carbon-based radicals, preferentially comprising from 6 to 20 carbon atoms, and of which at least one ring is aromatic; preferentially chosen from phenyl, biphenyl, naphthyl, indenyl, anthracenyl and tetrahydronaphthyl radicals; more preferentially, the aryl radicals of the invention are phenyl radicals.

The "heterocyclic" radicals are fused or non-fused, saturated or unsaturated, aromatic or non-aromatic, monocyclic or polycyclic, optionally cationic, 4- to 30-membered, preferentially 5- to 15-membered radicals, in at least one ring at least one ring member is a heteroatom, chosen in particular from O, N and S, preferably comprising from 1 to 6 heteroatoms, in particular O or N, optionally substituted with one or more atoms or groups as defined previously, especially one or more alkyl, alkoxy, carboxyl, hydroxyl, amine or oxo groups.

The "heteroaryl" radicals are fused or non-fused, preferentially 5- to 22-membered monocyclic or polycyclic radicals, comprising from 1 to 6 heteroatoms chosen from nitrogen, oxygen and sulfur atoms, and at least one ring of which is aromatic; preferentially, the heteroaryl radicals are chosen from acridinyl, benzimidazolyl, benzobistriazolyl, benzopyrazolyl, benzopyridazinyl, benzoquinolyl, benzothiazolyl, benzotriazolyl, benzoxazolyl, pyridyl, tetrazolyl, dihydrothiazolyl, imidazopyridyl, imidazolyl, indolyl, isoquinolyl, naphthoimidazolyl, naphthooxazolyl, naphthopyrazolyl, oxadiazolyl, oxazolyl, oxazolopyridyl, phenazinyl, phenoxazolyl, pyrazinyl, pyrazolyl, pyrilyl, pyrazoyltriazyl, pyridyl, pyridinoimidazolyl, pyrrolyl, quinolyl, tetrazolyl, thiadiazolyl, thiazolyl, thiazolopyridyl, thiazoylimidazolyl, thiopyrylyl, triazolyl, xanthyl and the ammonium salts thereof.

Among the heterocyclic radicals that may be used in the invention, mention may be made particularly of furyl, pyranyl, pyrrolyl, piperazinyl, piperidyl, morpholinyl, imidazolyl, pyrazolyl, pyridyl and thienyl groups. Preferably, the heterocyclic groups are fused heteroaryl groups such as benzofuryl, chromenyl, xanthenyl, indolyl, isoindolyl, quinolyl, isoquinolyl, chromanyl, isochromanyl, indolinyl, isoindolinyl, coumarinyl or isocoumarinyl groups, these groups possibly being substituted, in particular with one or more non-adjacent hydroxyl groups.

The "heterocycloalkyl" radicals are saturated heterocyclic radicals as defined previously, such as tetrahydrofuryl, tetrahydropyranyl, piperazinyl, piperidyl or morpholinyl.

The cycloalkyl radicals are cyclic radicals as defined previously, preferably saturated $C_4$-$C_8$ monocyclic radicals, such as cyclobutyl, cyclopentyl or cyclohexyl. The cycloalkyl radicals may be substituted, in particular with alkyl, alkoxy, carboxylic acid, hydroxyl, amine and ketone groups.

The term "anionic counterion" means an anion or an anionic group derived from an organic or mineral acid salt which counterbalances the cationic charge of the dye; more particularly, the anionic counterion is chosen from: i) halides such as chloride or bromide; ii) nitrates; iii) sulfonates, including $C_1$-$C_6$ alkylsulfonates: Alk-$S(O)_2O^-$ such as methanesulfonate or mesylate and ethanesulfonate; iv) arylsulfonates: Ar—$S(O)_2O^-$ such as benzenesulfonate and toluenesulfonate or tosylate; v) citrate; vi) succinate; vii) tartrate; viii) lactate; ix) alkyl sulfates: Alk-O—$S(O)O^-$ such as methyl sulfate and ethyl sulfate; x) aryl sulfates: Ar—O—$S(O)O^-$ such as benzene sulfate and toluene sulfate; xi) alkoxy sulfates: Alk-O—$S(O)_2O^-$ such as methoxy sulfate and ethoxy sulfate; xii) aryloxy sulfates: Ar—O—$S(O)_2O^-$, xiii) phosphates $O=P(OH)_2$—$O^-$, $O=P(O^-)_2$—OH $O=P(O^-)_3$, HO—$[P(O)(O^-)]_w$—$P(O)(O^-)_2$ with w being an integer; xiv) acetate; xv) triflate; and xvi) borates such as tetrafluoroborate, xvii) disulfate $(O=)_2S(O^-)_2$ or $SO_4^{2-}$ and monosulfate $HSO_4^-$.

The anionic counterion, derived from the organic or mineral acid salt, ensures the electrical neutrality of the molecule; thus, it is understood that when the anion comprises several anionic charges, then the same anion may serve for the electrical neutrality of several cationic groups in the same molecule or else may serve for the electrical neutrality of several molecules; for example, a disulfide dye of formula (I) which contains two cationic chromophores may contain either two "singly charged" anionic counterions or a "doubly charged" anionic counterion such as $(O=)_2S(O^-)_2$ or $O=P(O^-)_2$—OH.

The nitrogenous heterocycle formed by $R_1$ and $R_6$ may contain one or more other heteroatoms, especially a heteroatom chosen from N, O and S, one or more groups S(O), $S(O)_2$ and C(O), and combinations thereof. Said heterocycle may moreover be substituted as described above.

In formulae (I) and (II) above, when $R_1$ and/or $R_6$ represent a substituted alkyl radical, then the substituents are especially chosen from halogen atoms, —OH, —$OR_9$, —$NH_2$, —$N(H)R_{10}$ or —$N(R_{11})R_{12}$ radicals, saturated or unsaturated cyclic radicals optionally containing a heteroatom chosen from N, S and O, the ring itself possibly being substituted, in which $R_9$, $R_{10}$, $R_{11}$ and $R_{12}$, which may be identical or different, are as defined previously.

According to a particular embodiment of the invention, the compounds of formula (I) or (II) above are such that $Z_1$ represents an oxygen atom, a radical —$N(R_6)$— or a radical —$N(R_6)$— forming with $R_1$ a heterocycle, the radical $R_6$ possibly being chosen from a hydrogen atom, a $C_1$-$C_6$ alkyl radical and a $C_1$-$C_6$ alkyl radical substituted with a hydroxyl radical, an amino radical, a ($C_1$-$C_4$)alkylamino radical, a di($C_1$-$C_4$)alkylamino radical, or a $C_1$-$C_6$ alkyl radical which is itself substituted with a nitrogenous heterocycle, for example piperazinyl, imidazolyl, pyrrolidinyl, pyridyl, morpholinyl or piperidyl.

According to this embodiment, $Z_1$ preferably represents an oxygen atom or a radical —N(H)—, and even more preferentially an oxygen atom.

According to another embodiment, $Z_1$ represents a radical —$NR_6$-forming with $R_1$ an optionally cationic heterocycle, such as piperazinyl, piperazinium, imidazolyl, pyrrolidinyl, pyridyl, morpholinyl, morpholinium, piperidyl or piperidinium, preferentially piperazinyl or piperazinium optionally substituted especially with one or more $C_1$-$C_4$ alkyl groups such as methyl.

According to the invention, the radical $R_1$ may be chosen from a $C_1$-$C_6$ alkyl radical, a $C_1$-$C_6$ alkyl radical substituted with one or more hydroxyl groups, a $C_1$-$C_6$ alkyl radical substituted with one or more amino groups such as (di)($C_1$-$C_4$ alkyl)amino, a $C_1$-$C_6$ alkyl radical substituted with a nitrogenous heterocycle, for example piperazinyl, imidazolyl, pyrrolidinyl, pyridyl, morpholinyl or piperidyl.

Preferably, the radical $R_1$ represents a $C_1$-$C_6$ alkyl radical, a $C_1$-$C_6$ alkyl radical substituted with a hydroxyl group, a $C_1$-$C_6$ alkyl radical substituted with a (di)($C_1$-$C_4$ alkyl)amino such as dimethylamino, a $C_1$-$C_6$ alkyl radical substituted with a nitrogenous heterocycle chosen from imidazolyl, pyrrolidinyl, piperidyl, morpholinyl and piperazinyl.

Even more preferentially, the radical $R_1$ represents a $C_1$-$C_6$ alkyl radical, a $C_1$-$C_6$ alkyl radical substituted with a hydroxyl group, a $C_1$-$C_6$ alkyl radical substituted with a (di)($C_1$-$C_4$ alkyl)amino such as dimethylamino or dimethylaminopropyl.

According to one embodiment, $R_1$ represents a $C_1$-$C_6$ alkyl radical substituted with a hydroxyl group such as the hydroxyethyl radical, or a $C_1$-$C_6$ alkyl radical substituted with a (di)($C_1$-$C_4$ alkyl)amino such as dimethylaminoethyl or dimethylaminopropyl.

According to the particular embodiment in which $R_1$ and $R_6$ together form a heterocycle with the nitrogen atom to which they are attached, then the heterocycle may be chosen from imidazoles, piperazines, pyrrolidines, piperidines and morpholines, these heterocycles possibly being substituted or unsubstituted.

When $R_2$, $R_3$, $R_4$ and $R_5$ represent a substituted alkyl radical, then this alkyl radical may especially be substituted with a group chosen from —OH, —$OR_9$, —$NH_2$, —N(H)$R_{10}$ and —N($R_{11}$)$R_{12}$ in which $R_9$, $R_{10}$, $R_{11}$ and $R_{12}$, which may be identical or different, are as defined previously.

By way of example, mention may be made of methyl, ethyl, hydroxyethyl, aminoethyl, propyl and butyl radicals.

According to a particular embodiment of the invention, the compounds of formulae (I) and (II) are such that $R_2$, $R_3$, $R_4$ and $R_5$ independently represent a hydrogen atom or a $C_1$-$C_4$ alkyl radical such as methyl, ethyl, propyl, isopropyl, butyl or tert-butyl.

According to a preferred embodiment of the invention, the compounds of formulae (I) and (II) are such that $R_2$, $R_3$, $R_4$ and $R_5$ represent a hydrogen atom.

According to a particular embodiment of the invention, the compounds of formulae (I) and (II) are such that $R'_2$ and $R'_3$ independently represent a hydrogen atom or a $C_1$-$C_6$ and preferably $C_1$-$C_4$ alkyl radical such as methyl, optionally substituted with one or more hydroxyl radicals.

According to a preferred embodiment of the invention, the compounds of formulae (I) and (II) are such that $R'_2$ and $R'_3$ independently represent a hydrogen atom or a $C_1$-$C_4$ alkyl radical such as methyl.

According to a particular embodiment of the invention, the compounds of formulae (I) and (II) are such that R' represents a hydrogen atom or a $C_1$-$C_4$ alkyl radical, preferably a hydrogen atom.

According to a particular embodiment, the compounds of formulae (I) and (II) are such that $R'_6$ represents a hydrogen atom; a linear or branched $C_1$-$C_6$ alkyl radical, optionally substituted with one or more radicals, which may be identical or different, chosen from —OH and —N($R'_7$)$R'_8$; a $C_{1-6}$ hydroxyalkoxy radical; a radical —O-Ak-N($R'_9$)—$R'_{10}$ in which Ak denotes a linear or branched, preferably linear, divalent $C_1$-$C_8$ alkylene radical with $R'_7$ and $R'_{10}$ independently denoting a hydrogen atom or a $C_1$-$C_4$ alkyl radical optionally substituted with a hydroxyl radical;

$R'_9$ and $R'_{10}$ independently denoting a linear or branched $C_1$-$C_4$ alkyl radical; or alternatively $R'_9$ and $R'_{10}$ form, together with the nitrogen atom that bears them, a saturated or unsaturated 5- to 8-membered heterocycle, one of the chain members possibly being an oxygen or nitrogen atom or a radical $NR'_{11}$ with $R'_{11}$ representing a hydrogen atom or a $C_1$-$C_4$ alkyl group, optionally substituted with one or more radicals chosen from —OH, —$NR'_7R'_8$ and $C_1$-$C_4$ alkyls.

According to a preferred embodiment of the invention, the compounds of formulae (I) and (II) are such that $R'_6$ represents i) a hydrogen atom; ii) a linear or branched $C_1$-$C_6$ alkyl radical, optionally substituted with a hydroxyl radical; iii) a $C_{1-6}$ hydroxyalkoxy radical; iv) a radical —O-Ak-$NR'_9R'_{10}$ in which Ak denotes a linear divalent $C_1$-$C_8$ alkylene radical with:

$R'_9$ and $R'_{10}$ independently denoting a saturated, linear or branched $C_1$-$C_4$ alkyl radical; or alternatively $R'_9$ and $R'_{10}$ form, together with the nitrogen atom that bears them, a heterocycle chosen from pyrrolidinyl, morpholinyl, imidazolyl, piperazinyl and piperidyl, said heterocycle being optionally substituted with one or more radicals chosen from —OH and $C_1$-$C_4$ alkyl such as methyl; preferably, said heterocycle is optionally substituted with a $C_1$-$C_4$ alkyl group such as methyl.

According to a particular embodiment of the invention, the compounds of formulae (I) and (II) are such that $R'_6$ represents a hydrogen atom; a linear $C_1$-$C_6$ alkyl radical; a $C_{1-6}$ hydroxyalkoxy radical; a radical —O-Ak-N($R'_9$)$R'_{10}$ in which Ak denotes a linear $C_1$-$C_6$ divalent alkylene radical, and $R'_9$ forms with $R'_{10}$ and the nitrogen atom that bears them a pyrrolidinyl, morpholinyl, imidazolyl, piperazinyl or piperidyl heterocycle, said heterocycle being optionally substituted with one or more $C_1$-$C_4$ alkyl radicals such as methyl.

According to another particular embodiment of the invention, the compounds of formulae (I) and (II) are such that R" represents a hydrogen atom or a linear $C_1$-$C_6$ alkyl radical, preferably a hydrogen atom or a saturated linear $C_1$-$C_4$ radical such as methyl.

Even more preferentially, the compounds according to the invention are chosen from the compounds of formulae (I) and (II), and also the optical isomer, geometrical isomer and tautomer forms thereof, the addition salts thereof with an acid or a base, and the solvates thereof such as hydrates:

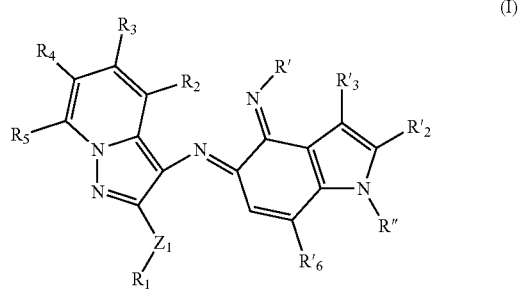

(I)

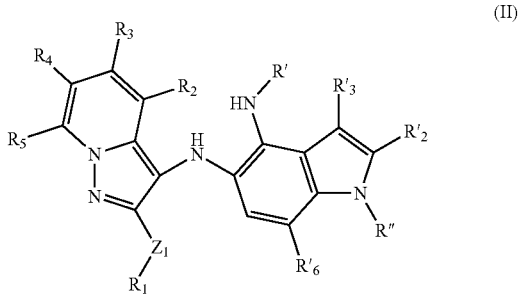

(II)

in which formulae (I) and (II):
$R_1$=—$CH_2CH_2OH$, —$CH_2CH_2N(CH_3)_2$, —$CH_2CH_2CH_2N(CH_3)_2$ when $Z_1$=O,
$R_1$=—$CH_2CH_2N(CH_3)_2$, —$CH_2CH_2CH_2N(CH_3)_2$ when $Z_1$=—N($R_6$)— and
$R_6$ represents a hydrogen atom, R', $R_2$, $R_3$, $R_4$ and $R_5$ denote a hydrogen atom, $R'_2$, $R'_3$ and R", which may be identical or different, denote a hydrogen atom or a methyl radical, $R'_6$ denotes a hydrogen atom or a methyl, ethyl, —O—$(CH_2)_2$—OH, —O—$(CH_2)_3$—OH, —O—$(CH_2)_2$-Het or —O—$(CH_2)_3$-Het radical with Het representing a pyrrolidinyl or morpholino or imidazolyl or N-methylpiperazino or piperidino group.

The term "addition salts" means the salts of physiologically acceptable organic or mineral acids of the compounds of formula (I) and/or (II).

The dyes of azomethine type bearing a pyrazolopyridine unit of formula (I) and the leuco compounds corresponding to the compounds of formula (II) may be optionally salified with strong mineral acids, for instance HCl, HBr, HI, $H_2SO_4$ or $H_3PO_4$, or organic acids, for instance acetic acid, lactic acid, tartaric acid, citric acid, succinic acid, benzenesulfonic acid, para-toluenesulfonic acid, formic acid or methanesulfonic acid.

Moreover, the addition salts that may be used in the context of the invention are also chosen from addition salts with a cosmetically acceptable base such as basifying agents as defined below, for instance alkali metal hydroxides such as sodium hydroxide, potassium hydroxide, aqueous ammonia, amines or alkanolamines.

In the context of the invention, the term "derivative of formula (I) and/or (II)" means all mesomeric, tautomeric or optical or geometrical isomer forms.

They may also be in the form of solvates, for example a hydrate or a solvate of a linear or branched alcohol such as ethanol or isopropanol.

The present invention makes it possible in particular to rapidly obtain intense colourings, which are chromatic and/or natural and/or uniform from the root to the end and which withstand the various attacking factors to which hair may be subjected, especially shampoos and light, which can be faded out especially in reductive medium and in particular at acidic pH and by reducing the temperature, and then reformed just as quickly especially in oxidizing medium and in particular at alkaline pH and by increasing the temperature.

The compounds of leuco type of formula (II) are colourless or weakly coloured and the corresponding azomethine derivatives bearing a pyrazolopyridine unit of formula (I) are coloured and colouring species. It is possible to modify the structure of the compounds of formula (II) to obtain the compounds of formula (I) by adding an oxidizing agent, and, conversely, it is possible to modify the structure of the compounds of formula (I) to obtain the compounds of formula (II) by adding a reducing agent. This structural modification may be facilitated by modifying the pH and/or the temperature. The formation of the compounds of formula (II) is thus promoted by an acidic pH and/or a temperature reduction, whereas the formation of the compounds of formula (I) is promoted by a basic pH and/or a temperature increase. Such behaviour makes it possible especially to readily modify the colouring of keratin fibres.

As examples of dyes of azomethine type bearing a pyrazolopyridine unit of formula (I) and/or (II) according to the invention, mention may be made of the compounds presented below:

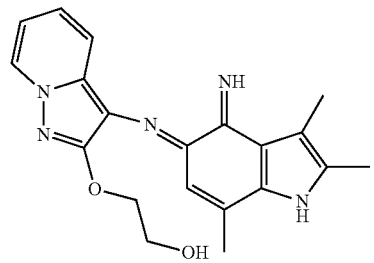

2-[(3-{[4-imino-2,3,7-trimethyl-1,4-dihydro-5H-indol-5-ylidene]amino}pyrazolo[1,5-a]pyridin-2-yl)oxy]ethanol

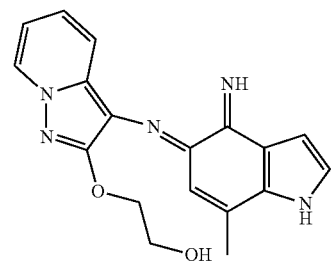

2-[(3-{[4-imino-7-methyl-1,4-dihydro-5H-indol-5-ylidene]amino}pyrazolo[1,5-a]pyridin-2-yl)oxy]ethanol

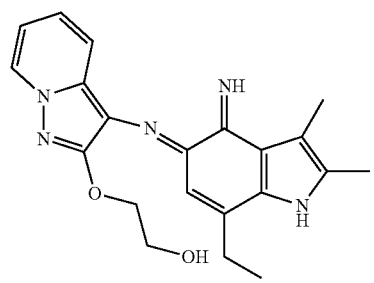

2-[(3-{[7-ethyl-4-imino-2,3-dimethyl-1,4-dihydro-5H-indol-5-ylidene]amino}pyrazolo[1,5-a]pyridin-2-yl)oxy]ethanol

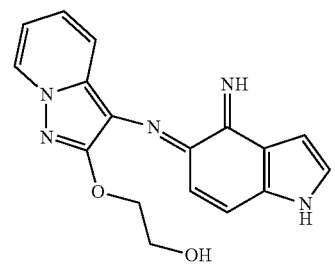

2-[(3-{[4-imino-1,4-dihydro-5H-indol-5-ylidene]amino}pyrazolo[1,5-a]pyridin-2-yl)oxy]ethanol

5

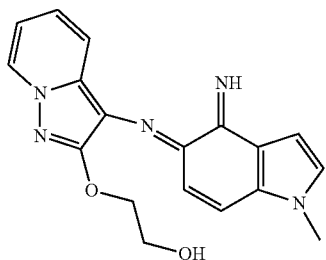

2-[(3-{[4-imino-1-methyl-1,4-dihydro-
5H-indol-5-
ylidene]amino}pyrazolo[1,5-a]pyridin-
2-yl)oxy]ethanol

6

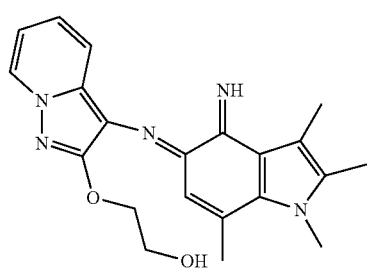

2-[(3-{[4-imino-1,2,3,7-
tetramethyl-1,4-dihydro-5H-indol-
5-ylidene]amino}pyrazolo[1,5-
a]pyridin-2-yl)oxy]ethanol

7

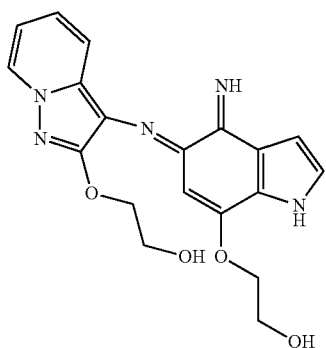

2-[(3-{[7-(2-hydroxyethoxy)-4-imino-
2,3-dimethyl-1,4-dihydro-5H-indol-5-
ylidene]amino}pyrazolo[1,5-
a]pyridin-2-yl)oxy]ethanol

8

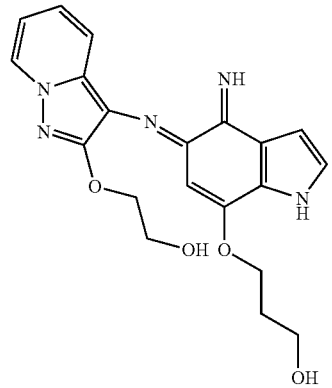

3-{[5-{[2-(2-
hydroxyethoxy)pyrazolo[1,5-
a]pyridin-3-yl]imino}-4-imino-4,5-
dihydro-1H-indol-7-yl]oxy}propan-
1-ol

9

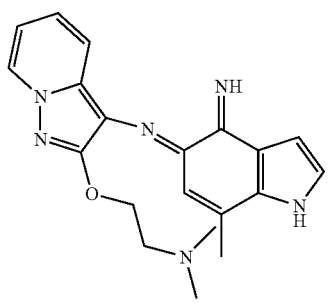

2-[2-(dimethylamino)ethoxy]-N-[-7-
ethyl-4-imino-2,3-dimethyl-1,4-
dihydro-5H-indol-5-
ylidene]pyrazolo[1,5-a]pyridin-3-amine

10

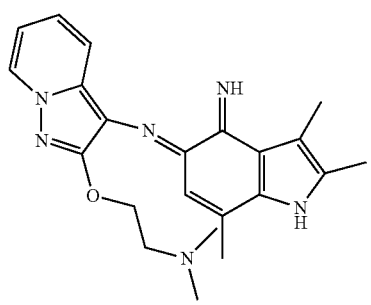

2-[2-(dimethylamino)ethoxy]-N-[7-
ethyl-4-imino-1,4-dihydro-5H-
indol-5-ylidene]pyrazolo[1,5-
a]pyridin-3-amine

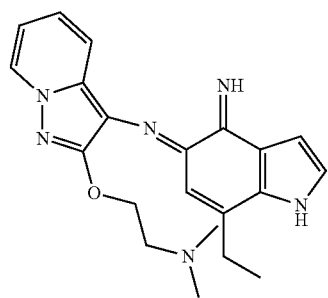

2-[2-(dimethylamino)ethoxy]-N-[-7-
ethyl-4-imino-1,4-dihydro-5H-indol-5-
ylidene]pyrazolo[1,5-a]pyridin-3-amine

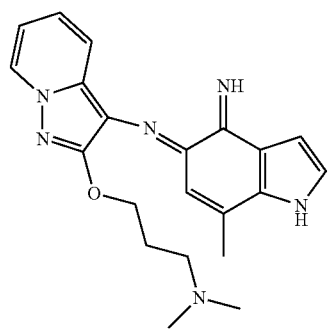

2-[3-(dimethylamino)propoxy]-N-
[4-imino-7-methyl-1,4-dihydro-5H-
indol-5-ylidene]pyrazolo[1,5-
a]pyridin-3-amine

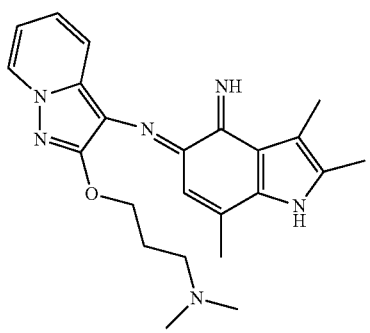

2-[3-(dimethylamino)propoxy]-N-[4-
imino-2,3,7-trimethyl-1,4-dihydro-5H-
indol-5-ylidene]pyrazolo[1,5-a]pyridin-
3-amine

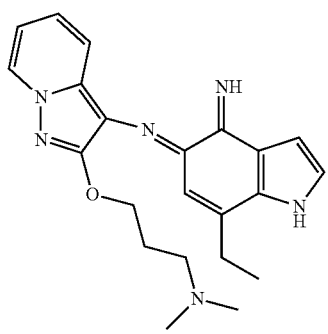

2-[3-(dimethylamino)propoxy]-N-
[7-ethyl-4-imino-1,4-dihydro-5H-
indol-5-ylidene]pyrazolo[1,5-
a]pyridin-3-amine

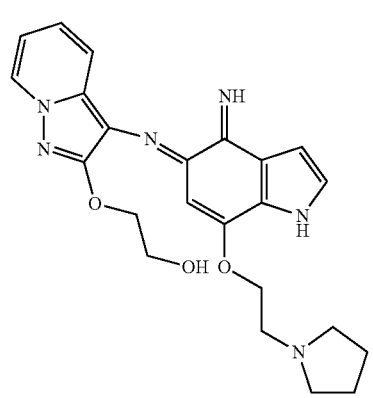

2-{[3-({4-imino-7-[2-(pyrrolidin-1-
yl)ethoxy]-1,4-dihydro-5H-indol-5-
ylidene}amino)pyrazolo[1,5-a]pyridin-
2-yl]oxy}ethanol

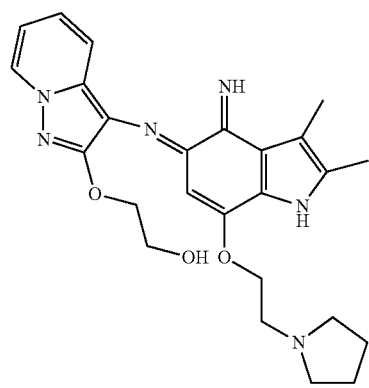

2-{[3-({4-imino-2,3-dimethyl-7-[2-
(pyrrolidin-1-yl)ethoxy]-1,4-
dihydro-5H-indol-5-
ylidene}amino)pyrazolo[1,5-
a]pyridin-2-yl]oxy}ethanol

17

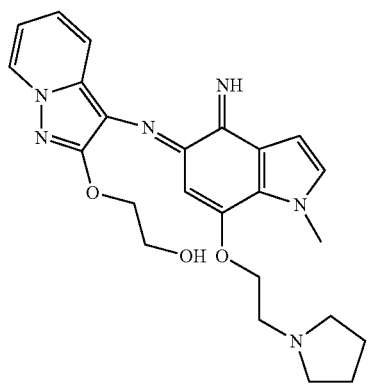

2-{[3-({4-imino-1-methyl-7-[2-(pyrrolidin-1-yl)ethoxy]-1,4-dihydro-5H-indol-5-ylidene}amino)pyrazolo[1,5-a]pyridin-2-yl]oxy}ethanol

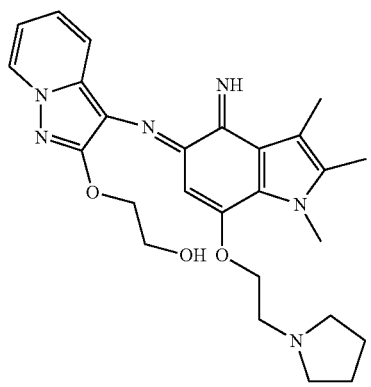

2-{[3-({4-imino-1,2,3-trimethyl-7-[2-(pyrrolidin-1-yl)ethoxy]-1,4-dihydro-5H-indol-5-ylidene}amino)pyrazolo[1,5-a]pyridin-2-yl]oxy}ethanol

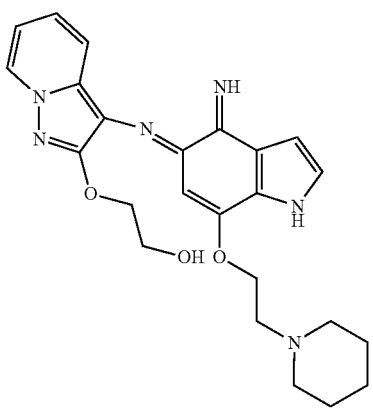

2-{[3-({4-imino-7-[2-(piperidin-1-yl)ethoxy]-1,4-dihydro-5H-indol-5-ylidene}amino)pyrazolo[1,5-a]pyridin-2-yl]oxy}ethanol

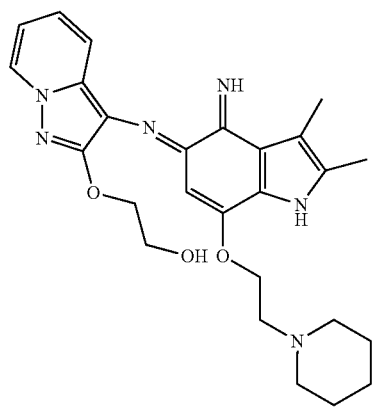

2-{[3-({4-imino-2,3-dimethyl-7-[2-(piperidin-1-yl)ethoxy]-1,4-dihydro-5H-indol-5-ylidene}amino)pyrazolo[1,5-a]pyridin-2-yl]oxy}ethanol

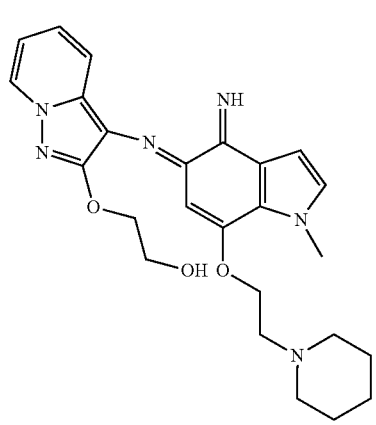

2-{[3-({4-imino-1-methyl-7-[2-(piperidin-1-yl)ethoxy]-1,4-dihydro-5H-indol-5-ylidene}amino)pyrazolo[1,5-a]pyridin-2-yl]oxy}ethanol

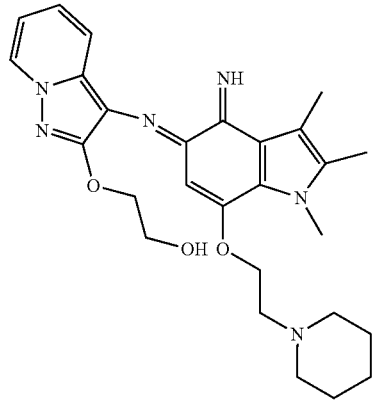

2-{[3-({4-imino-1,2,3-trimethyl-7-[2-(piperidin-1-yl)ethoxy]-1,4-dihydro-5H-indol-5-ylidene}amino)pyrazolo[1,5-a]pyridin-2-yl]oxy}ethanol

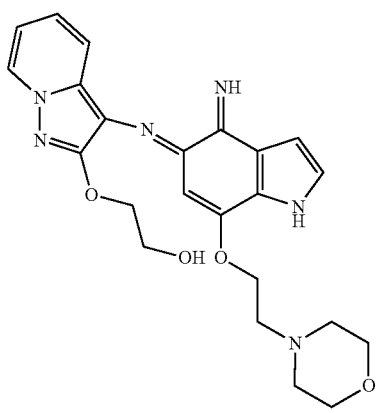

23

2-{[3-({4-imino-7-[2-(morpholin-4-
yl)ethoxy]-1,4-dihydro-5H-indol-5-
ylidene}amino)pyrazolo[1,5-a]pyridin-
2-yl]oxy}ethanol

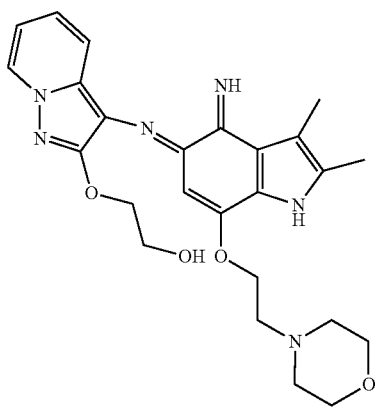

24

2-{[3-({4-imino-2,3-dimethyl-7-[2-
(morpholin-4-yl)ethoxy]-1,4-
dihydro-5H-indol-5-
ylidene}amino)pyrazolo[1,5-
a]pyridin-2-yl]oxy}ethanol

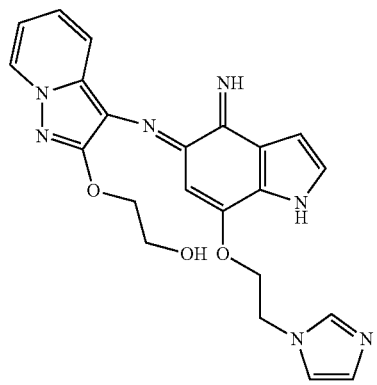

25

2-{[3-({7-[2-(1H-imidazol-1-
yl)ethoxy]-4-imino-1,4-dihydro-5H-
indol-5-ylidene}amino)pyrazolo[1,5-
a]pyridin-2-yl]oxy}ethanol

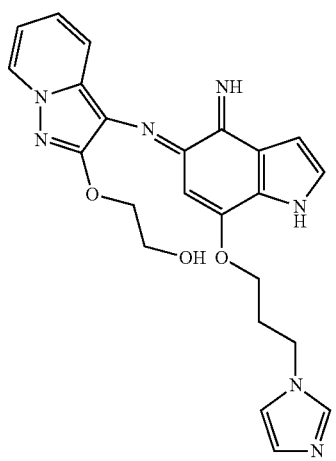

26

2-{[3-({7-[3-(1H-imidazol-1-
yl)propoxy]-4-imino-1,4-dihydro-
5H-indol-5-
ylidene}amino)pyrazolo[1,5-
a]pyridin-2-yl]oxy}ethanol

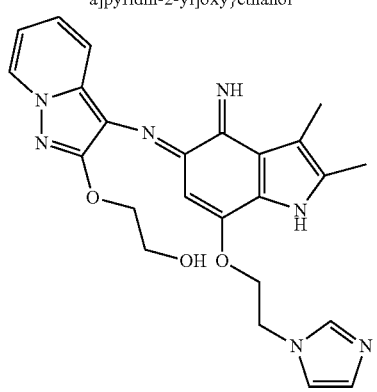

27

2-{[3-({7-[2-(1H-imidazol-1-
yl)ethoxy]-4-imino-2,3-dimethyl-1,4-
dihydro-5H-indol-5-
ylidene}amino)pyrazolo[1,5-a]pyridin-
2-yl]oxy}ethanol

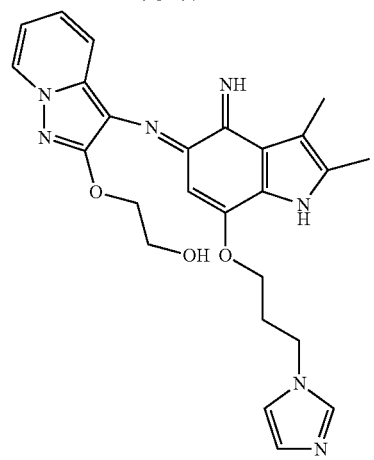

28

2-{[3-({7-[3-(1H-imidazol-1-
yl)propoxy]-4-imino-2,3-dimethyl-
1,4-dihydro-5H-indol-5-
ylidene}amino)pyrazolo[1,5-
a]pyridin-2-yl]oxy}ethanol

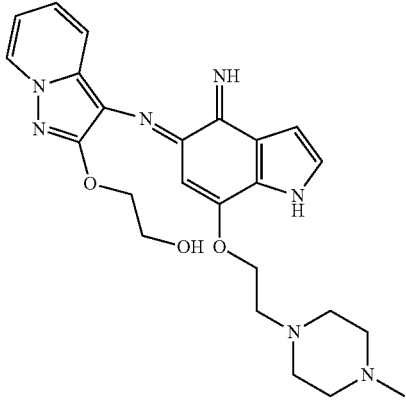

2-{[3-({4-imino-7-[2-(4-methylpiperazin-1-yl)ethoxy]-1,4-dihydro-5H-indol-5-ylidene}amino)pyrazolo[1,5-a]pyridin-2-yl]oxy}ethanol

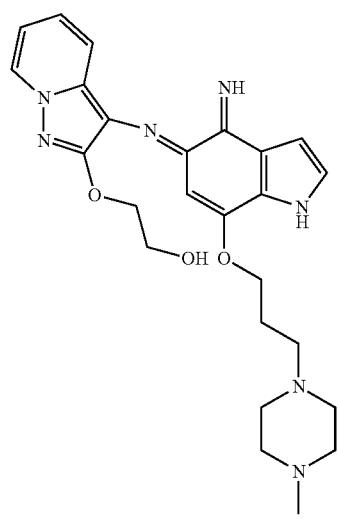

2-{[3-({4-imino-7-[3-(4-methylpiperazin-1-yl)propoxy]-1,4-dihydro-5H-indol-5-ylidene}amino)pyrazolo[1,5-a]pyridin-2-yl]oxy}ethanol

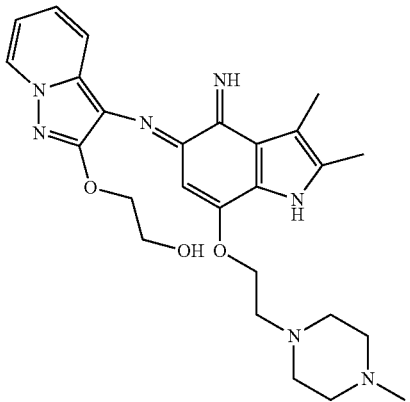

2-{[3-({4-imino-2,3-dimethyl-7-[2-(4-methylpiperazin-1-yl)ethoxy]-1,4-dihydro-5H-indol-5-ylidene}amino)pyrazolo[1,5-a]pyridin-2-yl]oxy}ethanol

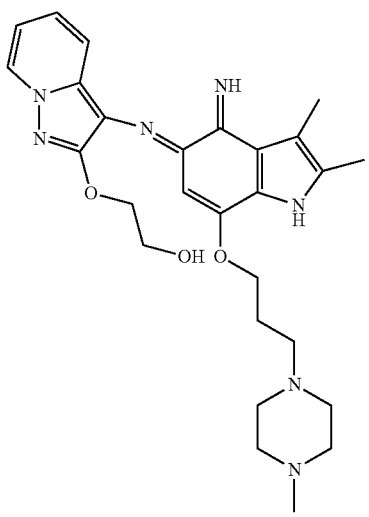

2-{[3-({4-imino-2,3-dimethyl-7-[3-(4-methylpiperazin-1-yl)propoxy]-1,4-dihydro-5H-indol-5-ylidene}amino)pyrazolo[1,5-a]pyridin-2-yl]oxy}ethanol

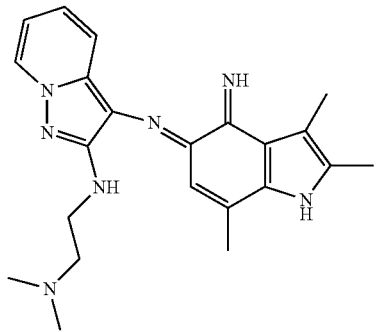

N2-[2-(dimethylamino)ethyl]-N3-[4-imino-2,3,7-trimethyl-1,4-dihydro-5H-indol-5-ylidene]pyrazolo[1,5-a]pyridine-2,3-diamine

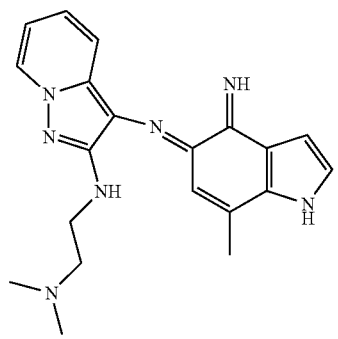

34

N2-[2-(dimethylamino)ethyl]-N3-
[4-imino-7-methyl-1,4-dihydro-5H-
indol-5-ylidene]pyrazolo[1,5-
a]pyridine-2,3-diamine

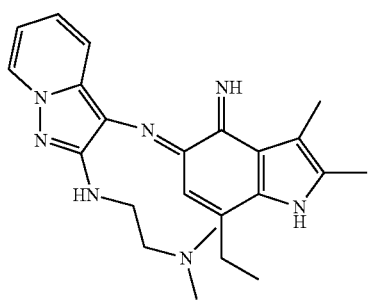

35

N2-[2-(dimethylamino)ethyl]-N3-[7-
ethyl-4-imino-2,3-dimethyl-1,4-
dihydro-5H-indol-5-
ylidene]pyrazolo[1,5-a]pyridine-2,3-
diamine

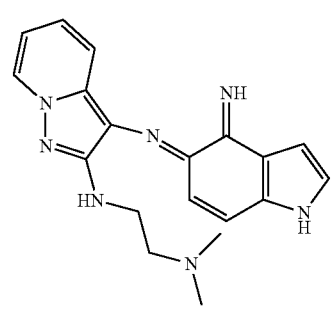

36

N2-[2-(dimethylamino)ethyl]-N3-
[4-imino-1,4-dihydro-5H-indol-5-
ylidene]pyrazolo[1,5-a]pyridine-
2,3-diamine

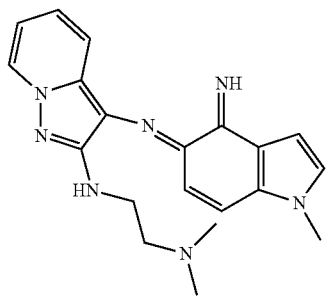

37

N2-[2-(dimethylamino)ethyl]-N3-[4-
imino-1-methyl-1,4-dihydro-5H-indol-
5-ylidene]pyrazolo[1,5-a]pyridine-2,3-
diamine

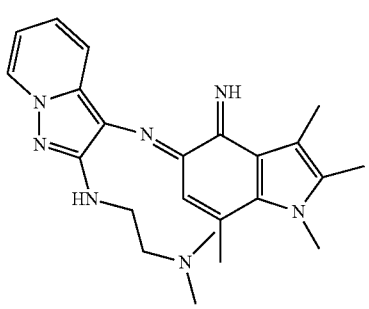

38

N2-[2-(dimethylamino)ethyl]-N3-
[4-imino-1,2,3,7-tetramethyl-1,4-
dihydro-5H-indol-5-
ylidene]pyrazolo[1,5-a]pyridine-
2,3-diamine

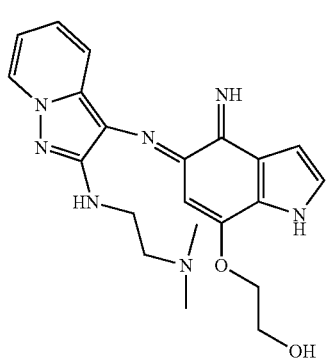

39

2-({5-[(2-{[2-
(dimethylamino)ethyl]amino}pyrazolo[
1,5-a]pyridin-3-yl)imino]-4-imino-4,5-
dihydro-1H-indol-7-yl}oxy)ethanol

40

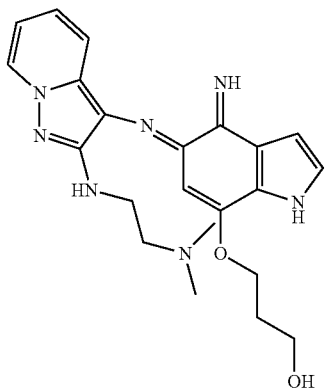

3-({5-[(2-{[2-(dimethylamino)ethyl]amino}pyrazolo[1,5-a]pyridin-3-yl)imino]-4-imino-4,5-dihydro-1H-indol-7-yl}oxy)propan-1-ol

41

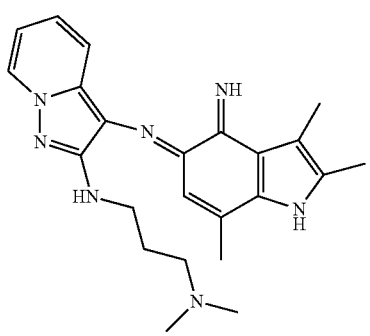

2-[3-(dimethylamino)propoxy]-N-[4-imino-2,3,7-trimethyl-1,4-dihydro-5H-indol-5-ylidene]pyrazolo[1,5-a]pyridin-3-amine

42

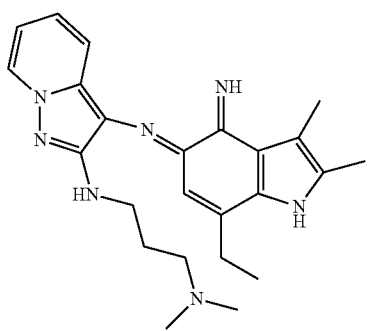

2-[3-(dimethylamino)propoxy]-N-[7-ethyl-4-imino-1,4-dihydro-5H-indol-5-ylidene]pyrazolo[1,5-a]pyridin-3-amine

43

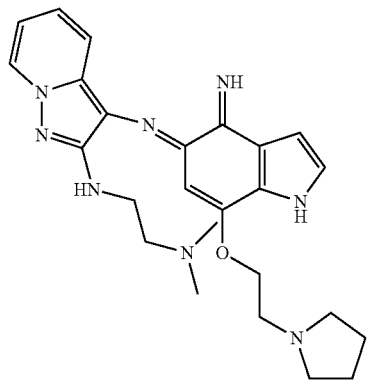

N2-[2-(dimethylamino)ethyl]-N3-{4-imino-7-[2-(pyrrolidin-1-yl)ethoxy]-1,4-dihydro-5H-indol-5-ylidene}pyrazolo[1,5-a]pyridine-2,3-diamine

44

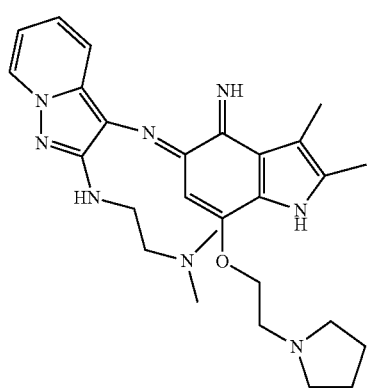

N2-[2-(dimethylamino)ethyl]-N3-{4-imino-2,3-dimethyl-7-[2-(pyrrolidin-1-yl)ethoxy]-1,4-dihydro-5H-indol-5-ylidene}pyrazolo[1,5-a]pyridine-2,3-diamine

45

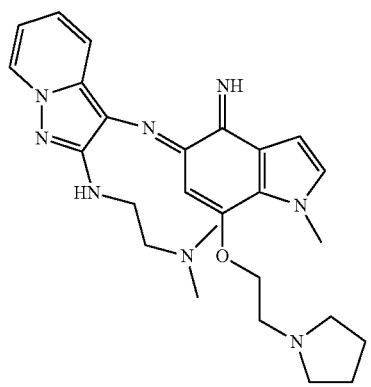

N2-[2-(dimethylamino)ethyl]-N3-{4-imino-1-methyl-7-[2-(pyrrolidin-1-yl)ethoxy]-1,4-dihydro-5H-indol-5-ylidene}pyrazolo[1,5-a]pyridine-2,3-diamine

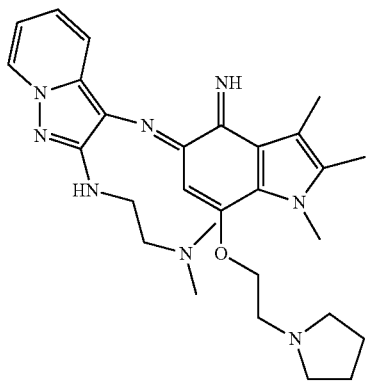

46

N2-[2-(dimethylamino)ethyl]-N3-
{4-imino-1,2,3-trimethyl-7-[2-
(pyrrolidin-1-yl)ethoxy]-1,4-
dihydro-5H-indol-5-
ylidene}pyrazolo[1,5-a]pyridine-
2,3-diamine

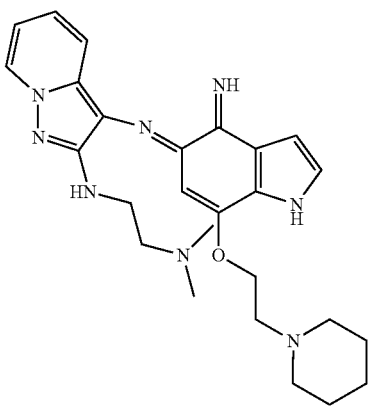

47

N2-[2-(dimethylamino)ethyl]-N3-{4-
imino-7-[2-(piperidin-1-yl)ethoxy]-1,4-
dihydro-5H-indol-5-
ylidene}pyrazolo[1,5-a]pyridine-2,3-
diamine

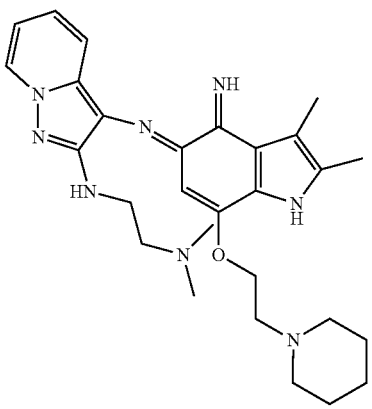

48

N2-[2-(dimethylamino)ethyl]-N3-
{4-imino-2,3-dimethyl-7-[2-
(piperidin-1-yl)ethoxy]-1,4-
dihydro-5H-indol-5-
ylidene}pyrazolo[1,5-a]pyridine-
2,3-diamine

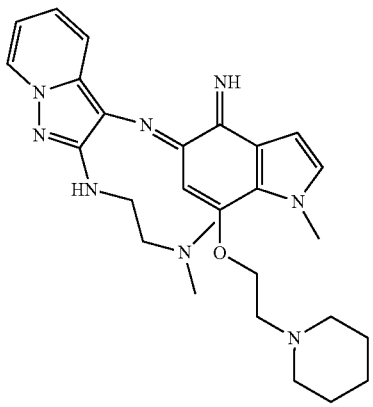

49

N2-[2-(dimethylamino)ethyl]-N3-{4-
imino-1-methyl-7-[2-(piperidin-1-
yl)ethoxy]-1,4-dihydro-5H-indol-5-
ylidene}pyrazolo[1,5-a]pyridine-2,3-
diamine

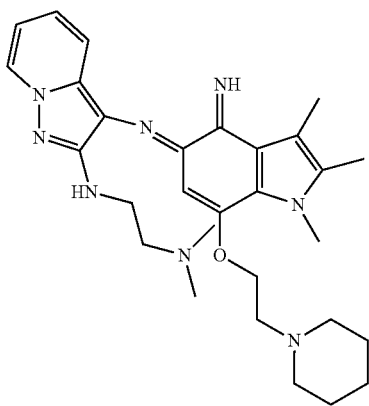

50

N2-[2-(dimethylamino)ethyl]-N3-
{4-imino-1,2,3-trimethyl-7-[2-
(piperidin-1-yl)ethoxy]-1,4-
dihydro-5H-indol-5-
ylidene}pyrazolo[1,5-a]pyridine-
2,3-diamine

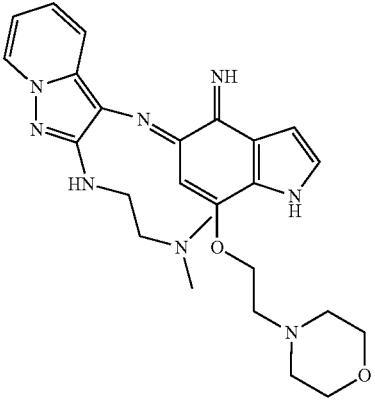

51

N2-[2-(dimethylamino)ethyl]-N3-{4-
imino-7-[2-(morpholin-4-yl)ethoxy]-
1,4-dihydro-5H-indol-5-
ylidene}pyrazolo[1,5-a]pyridine-2,3-
diamine

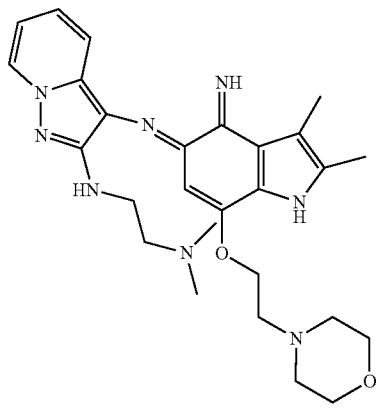

N2-[2-(dimethylamino)ethyl]-N3-{4-imino-2,3-dimethyl-7-[2-(morpholin-4-yl)ethoxy]-1,4-dihydro-5H-indol-5-ylidene}pyrazolo[1,5-a]pyridine-2,3-diamine

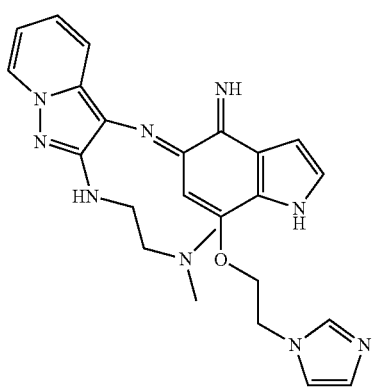

N2-[2-(dimethylamino)ethyl]-N3-{(5E)-7-[2-(1H-imidazol-1-yl)ethoxy]-4-imino-1,4-dihydro-5H-indol-5-ylidene}pyrazolo[1,5-a]pyridine-2,3-diamine

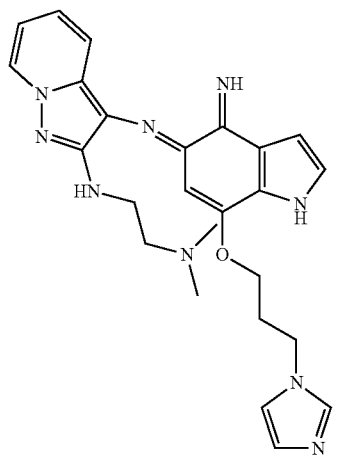

N2-[2-(dimethylamino)ethyl]-N3-{7-[3-(1H-imidazol-1-yl)propoxy]-4-imino-1,4-dihydro-5H-indol-5-ylidene}pyrazolo[1,5-a]pyridine-2,3-diamine

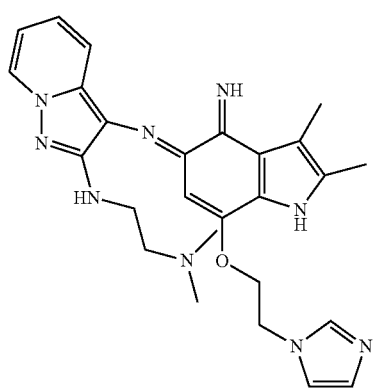

N2-[2-(dimethylamino)ethyl]-N3-{7-[2-(1H-imidazol-1-yl)ethoxy]-4-imino-2,3-dimethyl-1,4-dihydro-5H-indol-5-ylidene}pyrazolo[1,5-a]pyridine-2,3-diamine

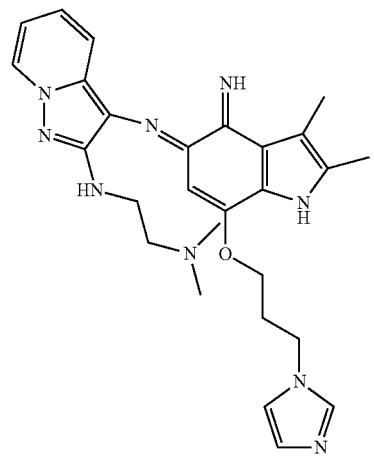

N2-[2-(dimethylamino)ethyl]-N3-{7-[3-(1H-imidazol-1-yl)propoxy]-4-imino-2,3-dimethyl-1,4-dihydro-5H-indol-5-ylidene}pyrazolo[1,5-a]pyridine-2,3-diamine

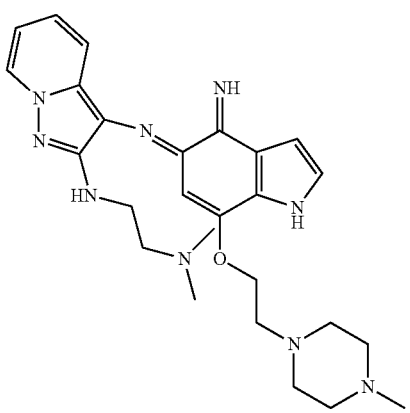

N2-[2-(dimethylamino)ethyl]-N3-{4-imino-7-[2-(4-methylpiperazin-1-yl)ethoxy]-1,4-dihydro-5H-indol-5-ylidene}pyrazolo[1,5-a]pyridine-2,3-diamine

58

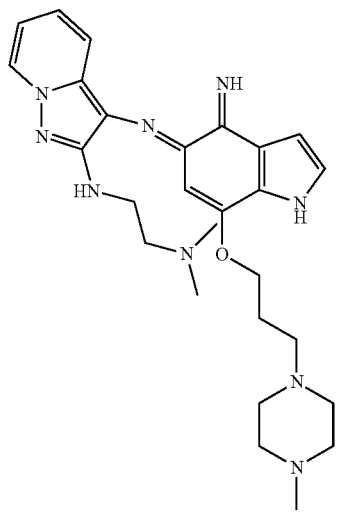

N2-[2-(dimethylamino)ethyl]-N3-
{4-imino-7-[3-(4-methylpiperazin-
1-yl)propoxy]-1,4-dihydro-5H-
indol-5-ylidene}pyrazolo[1,5-
a]pyridine-2,3-diamine

59

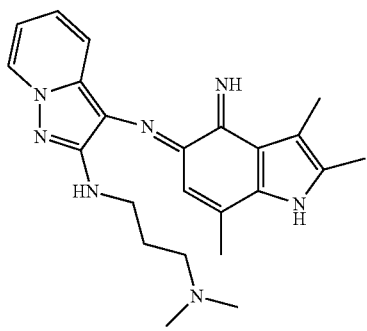

2-[3-(dimethylamino)propoxy]-N-[4-
imino-2,3,7-trimethyl-1,4-dihydro-5H-
indol-5-ylidene]pyrazolo[1,5-a]pyridin-
3-amine

60

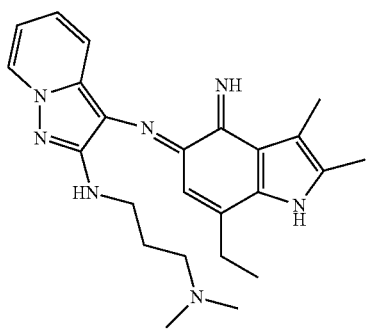

2-[3-(dimethylamino)propoxy]-N-
[7-ethyl-4-imino-1,4-dihydro-5H-
indol-5-ylidene]pyrazolo[1,5-
a]pyridin-3-amine

61

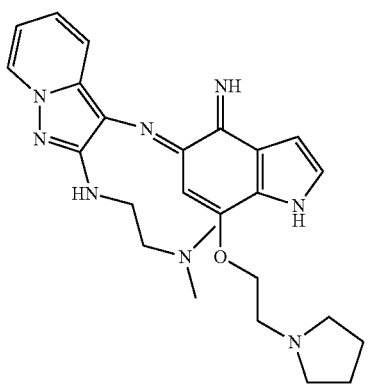

N2-[2-(dimethylamino)ethyl]-N3-{4-
imino-7-[2-(pyrrolidin-1-yl)ethoxy]-
1,4-dihydro-5H-indol-5-
ylidene}pyrazolo[1,5-a]pyridine-2,3-
diamine

62

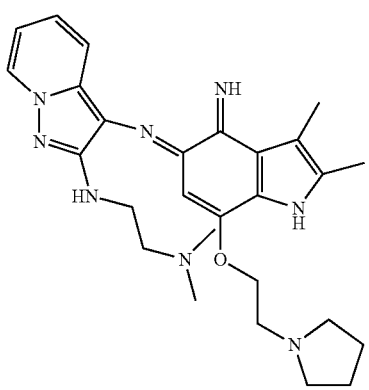

N2-[2-(dimethylamino)ethyl]-N3-
{4-imino-2,3-dimethyl-7-[2-
(pyrrolidin-1-yl)ethoxy]-1,4-
dihydro-5H-indol-5-
ylidene}pyrazolo[1,5-a]pyridine-
2,3-diamine

63

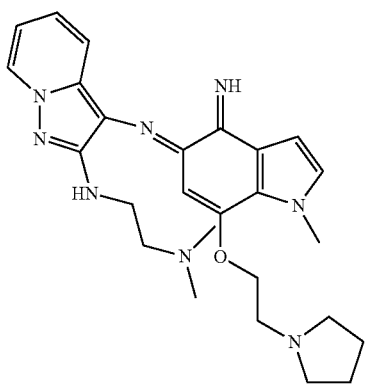

N2-[2-(dimethylamino)ethyl]-N3-{4-
imino-1-methyl-7-[2-(pyrrolidin-1-
yl)ethoxy]-1,4-dihydro-5H-indol-5-
ylidene}pyrazolo[1,5-a]pyridine-2,3-
diamine

64

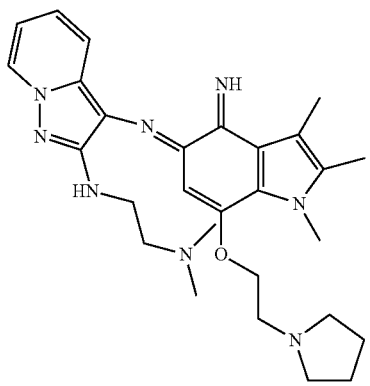

N2-[2-(dimethylamino)ethyl]-N3-
{4-imino-1,2,3-trimethyl-7-[2-
(pyrrolidin-1-yl)ethoxy]-1,4-
dihydro-5H-indol-5-
ylidene}pyrazolo[1,5-a]pyridine-
2,3-diamine

65

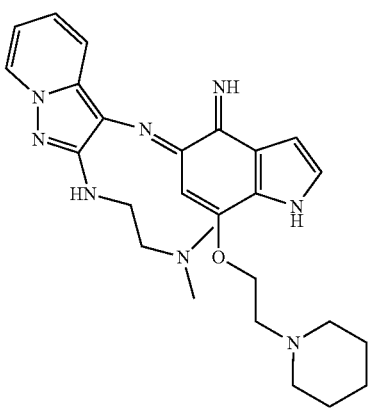

N2-[2-(dimethylamino)ethyl]-N3-{4-
imino-7-[2-(piperidin-1-yl)ethoxy]-1,4-
dihydro-5H-indol-5-
ylidene}pyrazolo[1,5-a]pyridine-2,3-
diamine

66

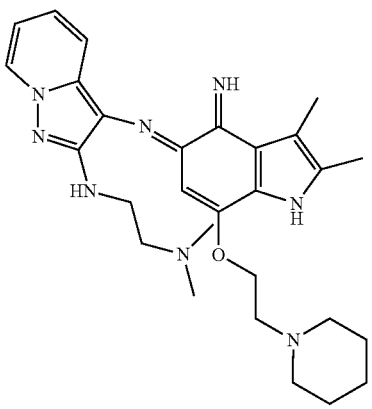

N2-[2-(dimethylamino)ethyl]-N3-
{4-imino-2,3-dimethyl-7-[2-
(piperidin-1-yl)ethoxy]-1,4-
dihydro-5H-indol-5-
ylidene}pyrazolo[1,5-a]pyridine-
2,3-diamine

67

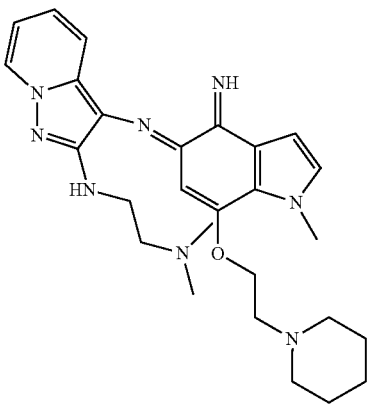

N2-[2-(dimethylamino)ethyl]-N3-{4-
imino-1-methyl-7-[2-(piperidin-1-
yl)ethoxy]-1,4-dihydro-5H-indol-5-
ylidene}pyrazolo[1,5-a]pyridine-2,3-
diamine

68

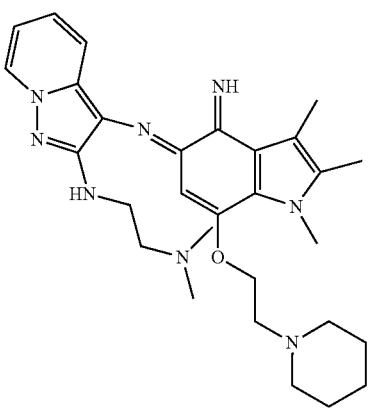

N2-[2-(dimethylamino)ethyl]-N3-
{4-imino-1,2,3-trimethyl-7-[2-
(piperidin-1-yl)ethoxy]-1,4-
dihydro-5H-indol-5-
ylidene}pyrazolo[1,5-a]pyridine-
2,3-diamine

69

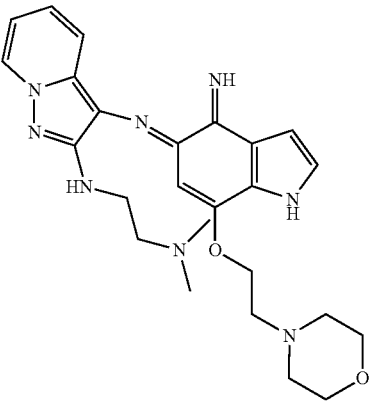

N2-[2-(dimethylamino)ethyl]-N3-{4-
imino-7-[2-(morpholin-4-yl)ethoxy]-
1,4-dihydro-5H-indol-5-
ylidene}pyrazolo[1,5-a]pyridine-2,3-
diamine

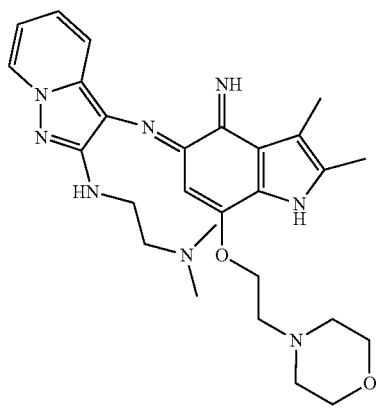

70

N2-[2-(dimethylamino)ethyl]-N3-
{4-imino-2,3-dimethyl-7-[2-
(morpholin-4-yl)ethoxy]-1,4-
dihydro-5H-indol-5-
ylidene}pyrazolo[1,5-a]pyridine-
2,3-diamine

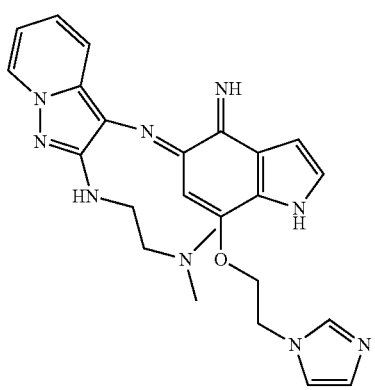

71

N2-[2-(dimethylamino)ethyl]-N3-{7-[2-
(1H-imidazol-1-yl)ethoxy]-4-imino-
1,4-dihydro-5H-indol-5-
ylidene}pyrazolo[1,5-a]pyridine-2,3-
diamine

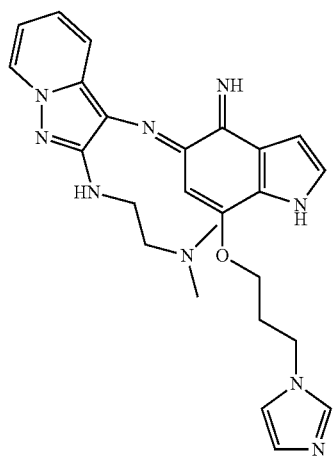

72

N2-[2-(dimethylamino)ethyl]-N3-
{7-[3-(1H-imidazol-1-yl)propoxy]-
4-imino-1,4-dihydro-5H-indol-5-
ylidene}pyrazolo[1,5-a]pyridine-
2,3-diamine

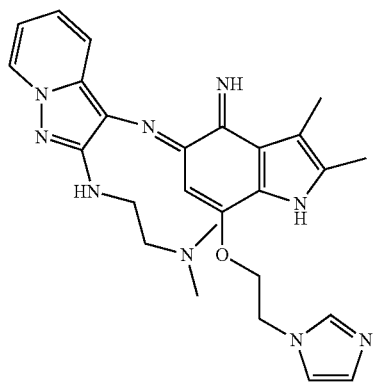

73

N2-[2-(dimethylamino)ethyl]-N3-{7-[2-
(1H-imidazol-1-yl)ethoxy]-4-imino-
2,3-dimethyl-1,4-dihydro-5H-indol-5-
ylidene}pyrazolo[1,5-a]pyridine-2,3-
diamine

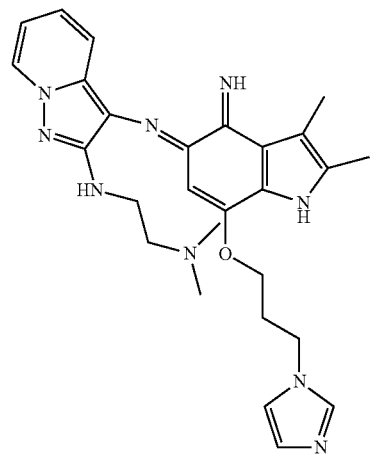

74

N2-[2-(dimethylamino)ethyl]-N3-
{7-[3-(1H-imidazol-1-yl)propoxy]-
4-imino-2,3-dimethyl-1,4-dihydro-
5H-indol-5-ylidene}pyrazolo[1,5-
a]pyridine-2,3-diamine

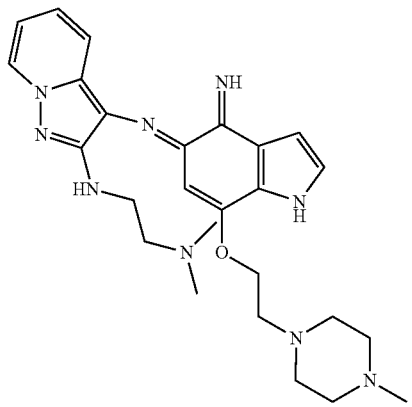

75

N2-[2-(dimethylamino)ethyl]-N3-{4-
imino-7-[2-(4-methylpiperazin-1-
yl)ethoxy]-1,4-dihydro-5H-indol-5-
ylidene}pyrazolo[1,5-a]pyridine-2,3-
diamine

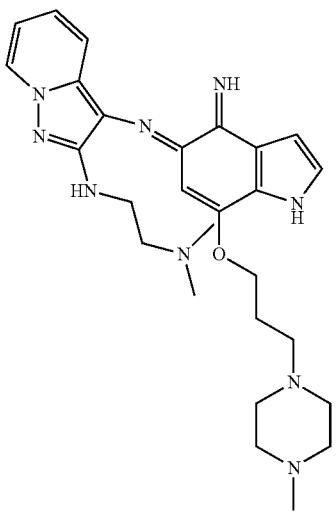

N2-[2-(dimethylamino)ethyl]-N3-
{4-imino-7-[3-(4-methylpiperazin-
1-yl)propoxy]-1,4-dihydro-5H-
indol-5-ylidene}pyrazolo[1,5-
a]pyridine-2,3-diamine and also the isomers, tautomers, mesomers, solvates and addition salts thereof.

Preferably, the dyes of azomethine type bearing a pyrazolopyridine unit of formula (I) are chosen from compounds 1 to 4 and 7 to 32, and also the isomers, mesomers, tautomers, solvates and addition salts thereof, and the corresponding leuco compounds.

Another subject of the invention is a process for preparing compounds of formulae (I) and (II) as defined previously, according to the following scheme:

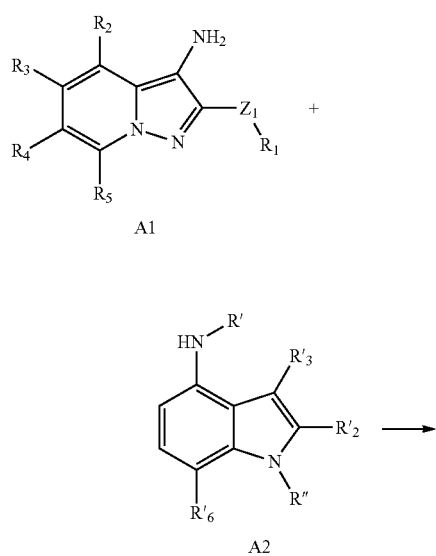

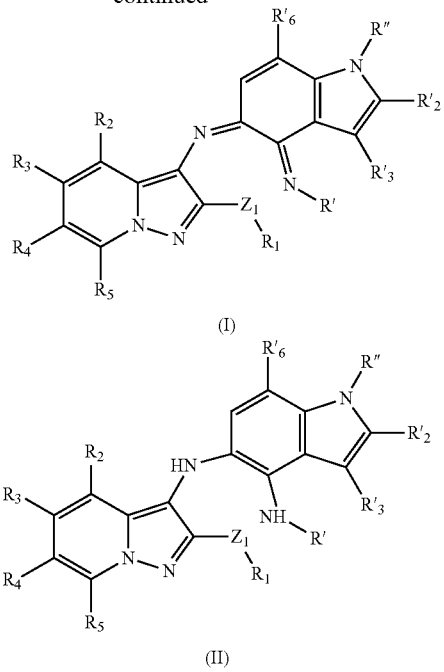

which consists:
in a first stage, in reacting a pyrazolo[1,5-a]pyridine compound A1 comprising an amino group in position 3 with an indole compound A2 which is free in position 5 and comprising in position 4 an amino group,
preferably, this reaction is performed i) in a polar protic solvent such as in water or a mixture of water/$C_1$-$C_{10}$ alcohol such as ethanol, ii) and/or in the presence of one or more basifying agents, as defined below, chosen in particular from sodium hydroxide, potassium hydroxide, a mineral carbonate such as potassium carbonate, or an acetate, iii) and/or in the presence of a chemical oxidizing agent such as peroxides or persulfates, iv) and/or at a temperature between room temperature, i.e. 25° C., and the reflux temperature of the solvent, preferably at room temperature, and then
in a second stage, in maintaining the reaction medium under stirring for a time of between 5 minutes and 48 hours, more particularly between 30 minutes and 24 hours if the reaction is performed at room temperature; and then
the reaction product (I) is optionally purified via a standard technique such as recrystallization, filtration or chromatography;
according to one variant, compound (I), once purified, is reduced using a reducing agent such as catalytic reduction with hydrogen borne on graphite, or using transition metals such as palladium or nickel, or alternatively by reduction with hydrides or borohydrides, or with thioglycolic acid derivatives, to give the leuco compound (II); optionally followed by a step of purification via a standard technique as mentioned previously to give the leuco compound (II);
according to another variant, compound (I) is not purified, and is reduced using a reducing agent as mentioned previously to give the leuco compound (II), optionally followed by a step of purification via a standard technique as mentioned previously.

More particularly, the compounds of formula (I) and/or (II) may be obtained according to the procedure described below.

In a reactor, compound A1 is dissolved in water and/or ethanol at room temperature. A2 is then added, followed by a base such as ammonia, sodium hydroxide, potassium hydroxide, a mineral carbonate such as potassium or ammonium carbonate, or an acetate in the presence of an oxidizing agent. The oxidizing agent may be air, aqueous hydrogen peroxide solution or any other chemical oxidizing agent. The reaction medium becomes coloured as soon as the last two reagents are added. The reaction medium thus obtained is stirred for a time of from 30 minutes to 24 hours. The product formed is filtered off and then washed with water and then optionally with isopropyl ether. The compound recovered in powder form is dried at 20° C. under vacuum to constant weight. In the case where there is no precipitation, the compound resulting from this reaction is recovered by evaporating off the solvent and optionally purified on a column of silica. The characterization is performed by NMR spectroscopy and/or mass spectrometry.

A subject of the present invention is also a composition for dyeing keratin fibres, comprising, in a medium that is suitable especially for dyeing keratin fibres such as the hair, at least one compound chosen from the compounds of formula (I) and/or (II) as defined previously, and also the optical isomers, geometrical isomers and tautomers thereof, and also the addition salts thereof with an acid or a base, and the solvates thereof such as hydrates.

According to a particular embodiment of the invention, the compounds of formula (I) or (II) as defined previously represent from 0.01% to 15% and more particularly from 0.05% to 10% by weight relative to the total weight of the composition.

The dye composition that is useful in the context of the invention may furthermore comprise an oxidation base. This oxidation base may be chosen from the oxidation bases conventionally used in oxidation dyeing, for example para-phenylenediamines, bis(phenyl)alkylenediamines, para-aminophenols, ortho-aminophenols and heterocyclic bases.

Among the para-phenylenediamines, examples that may be mentioned more particularly include para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl) amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene, 2-(2,5-diaminophenyl)ethanol, 2-(methoxymethyl)benzene-1,4-diamine, 3(-2,5-diaminophenyl)propan-1-ol and 1-{3-[(4-aminophenyl)amino]-propyl}-3-methyl-1H-imidazol-3-ium chloride, and the addition salts thereof with an acid.

Among the para-phenylenediamines mentioned above, para-phenylenediamine, para-tolylenediamine, 2-isopropyl-para-phenylenediamine, 2-β-hydroxyethyl-para-phenylenediamine, 2-β-hydroxyethyl-oxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-β-acetylaminoethyloxy-para-phenylenediamine, 2-(2,5-diaminophenyl)ethanol, 2-(methoxymethyl)benzene-1,4-diamine, 3(-2,5-diaminophenyl)propan-1-ol and 1-{3-[(4-aminophenyl)amino]-propyl}-3-methyl-1H-imidazol-3-ium chloride, and the addition salts thereof with an acid, are particularly preferred.

Among the bis(phenyl)alkylenediamines, examples that may be mentioned include N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)-tetramethylenediamine, N,N'-bis(4-methylaminophenyl)tetramethylenediamine, N,N'-bis(ethyl)-N,N'-bis(4'-amino3'-methylphenyl)ethylenediamine and 1,8-bis(2,5-diaminophenoxy)-3,6-dioxaoctane, and addition salts thereof with an acid.

Among the para-aminophenols that may be mentioned, for example, are para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethyl-phenol, 4-amino-2-aminomethylphenol, 4-amino-2-(β-hydroxyethylaminomethyl)phenol and 4-amino-2-fluorophenol, and addition salts thereof with an acid.

Among the ortho-aminophenols, examples that may be mentioned include 2-aminophenol, 2-amino-5-methylphenol, 2-amino-6-methylphenol and 5-acetamido-2-aminophenol, and addition salts thereof with an acid.

Among the heterocyclic bases, examples that may be mentioned include pyridine derivatives, pyrimidine derivatives and pyrazole derivatives, and derivatives of pyrazolo[1,2-a]pyrazol-1-one type and derivatives of pyrazolopyridine type as described in European patent applications Nos 1 792 903 and 1 792 606.

Among the pyridine derivatives, mention may be made of the compounds described, for example, in patents GB 1 026 978 and GB 1 153 196, for instance 2,5-diaminopyridine, 2-(4-methoxyphenyl)amino-3-aminopyridine, 2,3-diamino-6-methoxypyridine, 2-(β-methoxyethyl)-amino-3-amino-6-methoxypyridine and 3,4-diaminopyridine, and the addition salts thereof with an acid.

Among the pyrimidine derivatives, mention may be made of the compounds described, for example, in patents DE 2 359 399; JP 88-169 571; JP 05 163 124; EP 0 770 375 or patent application WO 96/15765, for instance 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and pyrazolopyrimidine derivatives such as those mentioned in patent application FR-A-2 750 048, and among which mention may be made of pyrazolo[1,5-a]pyrimidine-3,7-diamine, 2,5-dimethylpyrazolo[1,5-a]pyrimidine-3,7-diamine, pyrazolo[1,5-a]pyrimidine-3,5-diamine, 2,7-dimethylpyrazolo[1,5-a]pyrimidine-3,5-diamine, 3-aminopyrazolo[1,5-a]pyrimidin-7-ol, 3-aminopyrazolo[1,5-a]pyrimidin-5-ol, 2-(3-aminopyrazolo[1,5-a]pyrimidin-7-ylamino)ethanol, 2-(7-aminopyrazolo-[1,5-a]pyrimidin-3-ylamino)ethanol, 2-[(3-aminopyrazolo[1,5-a]-pyrimidin-7-yl)(2-hydroxyethyl)

amino]ethanol, 2-[(7-aminopyrazolo-[1,5-a]pyrimidin-3-yl) (2-hydroxyethyl)amino]ethanol, 5,6-dimethylpyrazolo[1,5-a]pyrimidine-3,7-diamine, 2,6-dimethylpyrazolo[1,5-a]-pyrimidine-3,7-diamine, 2,5,N7,N7-tetramethylpyrazolo[1,5-a]-pyrimidine-3,7-diamine and 3-amino-5-methyl-7-imidazolyl-propylaminopyrazolo[1,5-a]pyrimidine, and the addition salts thereof with an acid, and the tautomeric forms thereof, when a tautomeric equilibrium exists.

Among the pyrazole derivatives that may be mentioned are the compounds described in patents DE 3 843 892 and DE 4 133 957, and patent applications WO 94/08969, WO 94/08970, FR-A-2 733 749 and DE 195 43 988, for instance 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)-amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the addition salts thereof with an acid.

Among the derivatives of pyrazolo[1,2a]pyrazol-1-one type, mention may be made of compounds such as 2,3-diamino-6,7-dihydro, 1H-5H-pyrazolo[1,2a]pyrazol-1-one.

The dye composition that is useful in the context of the invention may also contain one or more couplers that are conventionally used for dyeing keratin fibres. Among these couplers, mention may be made especially of meta-phenylenediamines, meta-aminophenols, meta-diphenols, naphthalene-based couplers and heterocyclic couplers.

Examples that may be mentioned include 2-methyl-5-aminophenol, 5-N-(β-hydroxyethyl)amino-2-methylphenol, 6-chloro-2-methyl-5-aminophenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diamino-phenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine 3,5-diamino-2,6-dimethoxypyridine, 1-N-(β-hydroxyethyl)amino-3,4-methylenedioxybenzene and 2,6-bis(β-hydroxyethylamino)toluene, and the addition salts thereof with an acid.

In general, the addition salts with an acid that may be used in the context of the invention for the oxidation bases and the couplers are especially chosen from the hydrochlorides, hydrobromides, sulfates, citrates, succinates, tartrates, lactates, tosylates, benzenesulfonates, phosphates and acetates.

When they are present in the dye composition according to the invention, the oxidation base(s) are generally present in an amount ranging from 0.001% to 10% and more preferentially from 0.005% to 6% by weight relative to the total weight of the composition.

When they are present, the coupler(s) are generally present in an amount ranging from 0.001% to 10% and more preferentially from 0.005% to 6% by weight relative to the total weight of the composition.

The dye composition that is useful in the context of the invention may optionally comprise at least one additional direct dye conventionally used for the dyeing of keratin fibres. It may be chosen from cationic and nonionic species.

Non-limiting examples that may be mentioned include nitrobenzene dyes, azo, azomethine, methine, tetraazapentamethine, anthraquinone, naphthoquinone, benzoquinone, phenothiazine, indigoid, xanthene, phenanthridine and phthalocyanin dyes, triarylmethane-based dyes and natural dyes, alone or as mixtures.

It may be chosen, for example, from the following red or orange nitrobenzene dyes: 1-hydroxy-3-nitro-4-N-(γ-hydroxypropyl)-aminobenzene, N-(β-hydroxyethyl)amino-3-nitro-4-aminobenzene, 1-amino-3-methyl-4-N-(β-hydroxyethyl)amino-6-nitrobenzene, 1-hydroxy-3-nitro-4-N-(β-hydroxyethyl)aminobenzene, 1,4-diamino-2-nitrobenzene, 1-amino-2-nitro-4-methylaminobenzene, N-(β-hydroxyethyl)-2-nitro-para-phenylenediamine, 1-amino-2-nitro-4-(β-hydroxyethyl)amino-5-chlorobenzene, 2-nitro-4-aminodiphenylamine, 1-amino-3-nitro-6-hydroxybenzene, 1-(β-aminoethyl)amino-2-nitro-4-(β-hydroxyethyl-oxy)benzene, 1-(β,γ-dihydroxypropyl)oxy-3-nitro-4-(β-hydroxyethyl)-aminobenzene, 1-hydroxy-3-nitro-4-aminobenzene, 1-hydroxy-2-amino-4,6-dinitrobenzene, 1-methoxy-3-nitro-4-(β-hydroxyethyl)aminobenzene, 2-nitro-4'-hydroxydiphenylamine and 1-amino-2-nitro-4-hydroxy-5-methylbenzene.

The additional direct dye may also be chosen from yellow and green-yellow nitrobenzene direct dyes. Examples that may be mentioned include the compounds chosen from: 1-β-hydroxyethyloxy-3-methylamino-4-nitrobenzene, 1-methylamino-2-nitro-5-(β,γ-dihydroxy-propyl)oxybenzene, 1-(β-hydroxyethyl)amino-2-methoxy-4-nitrobenzene, 1-(β-aminoethyl)amino-2-nitro-5-methoxybenzene, 1,3-bis(β-hydroxyethyl)amino-4-nitro-6-chlorobenzene, 1-amino-2-nitro-6-methylbenzene, 1-(β-hydroxyethyl)amino-2-hydroxy-4-nitrobenzene, N-(β-hydroxyethyl)-2-nitro-4-trifluoromethylaniline, 4-(β-hydroxyethyl)-amino-3-nitrobenzenesulfonic acid, 4-ethylamino-3-nitrobenzoic acid, 4-(β-hydroxyethyl)amino-3-nitrochlorobenzene, 4-(β-hydroxyethyl)amino-3-nitromethylbenzene, 4-(β,γ-dihydroxypropyl)amino-3-nitrotrifluoro-methylbenzene, 1-(β-ureidoethyl)amino-4-nitrobenzene, 1,3-diamino-4-nitrobenzene, 1-hydroxy-2-amino-5-nitrobenzene, 1-amino-2-[tris(hydroxymethyl)methyl]amino-5-nitrobenzene, 1-(β-hydroxyethyl)-amino-2-nitrobenzene and 4-(β-hydroxyethyl)amino-3-nitrobenzamide.

Mention may also be made of blue or violet nitrobenzene direct dyes, for instance 1-(β-hydroxyethyl)amino-4-N,N-bis(β-hydroxyethyl)-amino-2-nitrobenzene, 1-(γ-hydroxypropyl)amino-4-N,N-bis(β-hydroxyethyl)amino-2-nitrobenzene, 1-(β-hydroxyethyl)amino-4-(N-methyl-N-β-hydroxyethyl)amino-2-nitrobenzene, 1-(β-hydroxyethyl)-amino-4-(N-ethyl-N-β-hydroxyethyl)amino-2-nitrobenzene, 1-(β,γ-dihydroxypropyl)amino-4-(N-ethyl-N-β-hydroxyethyl)amino-2-nitrobenzene, and the 2-nitro-para-phenylenediamines of formula (III) below:

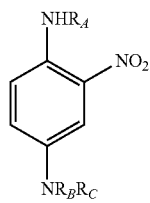

(III)

in which:
R_B represents a $C_1$-$C_4$ alkyl radical or a β-hydroxyethyl, β-hydroxypropyl or γ-hydroxypropyl radical;
R_A and R_C, which may be identical or different, represent a β-hydroxyethyl, β-hydroxypropyl, γ-hydroxypropyl or β,γ-dihydroxy-propyl radical, at least one of the radicals R_B, R_C or R_A representing a γ-hydroxypropyl radical and R_B and R_C not being able simultaneously to denote a β-hydroxyethyl radical when R_B is a γ-hydroxypropyl radical, such as those described in French patent FR 2 692 572.

Among the azo direct dyes that may be used according to the invention, mention may be made of the cationic azo dyes described in patent applications WO 95/15144, WO 95/01772, EP 714954, FR 2 822 696, FR 2 825 702, FR 2 825 625, FR 2 822 698, FR 2 822 693, FR 2 822 694, FR 2 829 926, FR 2 807 652, WO 02/078660, WO 02/100834, WO 02/100369 and FR 2 844 269.

Among these compounds, mention may be made most particularly of the following dyes: 1,3-dimethyl-2-[[4-(dimethylamino)phenyl]azo]-1H-imidazolium halides, 1,3-dimethyl-2-[(4-aminophenyl)azo]-1H-imidazolium halides, 1-methyl-4-[(methylphenylhydrazono)methyl]-pyridinium halides or alkyl sulfates.

Among the azo direct dyes, mention may also be made of the following dyes, described in the Colour Index International 3rd edition: Disperse Red 17, Acid Yellow 9, Acid Black 1, Basic Red 22, Basic Red 76, Basic Yellow 57, Basic Brown 16, Acid Yellow 36, Acid Orange 7, Acid Red 33, Acid Red 35, Basic Brown 17, Acid Yellow 23, Acid Orange 24, Disperse Black 9.

Mention may also be made of 1-(4'-aminodiphenylazo)-2-methyl-4-bis(β-hydroxyethyl)aminobenzene and 4-hydroxy-3-(2-methoxy-phenylazo)-1-naphthalenesulfonic acid.

Among the quinone direct dyes, mention may be made of the following dyes: Disperse Red 15, Solvent Violet 13, Acid Violet 43, Disperse Violet 1, Disperse Violet 4, Disperse Blue 1, Disperse Violet 8, Disperse Blue 3, Disperse Red 11, Acid Blue 62, Disperse Blue 7, Basic Blue 22, Disperse Violet 15, Basic Blue 99, and also the following compounds: 1-N-methylmorpholiniumpropylamino-4-hydroxyanthraquinone, 1-aminopropylamino-4-methylaminoanthraquinone, 1-aminopropylaminoanthraquinone, 5-β-hydroxyethyl-1,4-diamino-anthraquinone, 2-aminoethylaminoanthraquinone, 1,4-bis(β,γ-dihydroxypropylamino)anthraquinone.

Among the azine dyes, mention may be made of the following compounds: Basic Blue 17, Basic Red 2.

Among the triarylmethane dyes that may be used according to the invention, mention may be made of the following compounds: Basic Green 1, Acid Blue 9, Basic Violet 3, Basic Violet 14, Basic Blue 7, Acid Violet 49, Basic Blue 26, Acid Blue 7.

Among the indoamine dyes that may be used according to the invention, mention may be made of the following compounds: 2β-hydroxyethlyamino-5-[bis(β-4'-hydroxyethyl)amino]anilino-1,4-benzoquinone, 2β-hydroxyethylamino-5-(2'-methoxy-4'-amino)anilino-1,4-benzoquinone, 3-N-(2'-chloro-4'-hydroxy)phenylacetylamino-6-methoxy-1,4-benzoquinoneimine, 3-N(3'-chloro-4'-methylamino)-phenylureido-6-methyl-1,4-benzoquinoneimine and 3-[4'-N-(ethylcarbamylmethyl)amino]phenylureido-6-methyl-1,4-benzoquinoneimine.

Among the dyes of tetraazapentamethine type that may be used according to the invention, mention may be made of the following compounds: 2-((E)-{(E)-[(1,3-dimethyl-1,3-dihydro-2H-imidazol-2-ylidene)hydrazono]methyl}diazenyl)-1,3-dimethyl-1H-imidazol-3-ium chloride; 2-{(E)-[(1Z)—N-(1,3-dimethyl-1,3-dihydro-2H-imidazol-2-ylidene)ethanehydrazonoyl]diazenyl}-1,3-dimethyl-1H-imidazol-3-ium chloride; 4-methoxy-2-((E)-{(1E)-1-[(2E)-(4-methoxy-1-methylpyridin-2(1H)-ylidene)hydrazono]ethyl}diazenyl)-1-methylpyridinium chloride; 1-methyl-2-((E)-{(1E)-1-[(2E)-(1-methylpyridin-2(1H)-ylidene)-hydrazono]ethyl}diazenyl)pyridinium chloride; 1-(2-hydroxyethyl)-2-[(E)-((1E)-1-{(2E)-[1-(2-hydroxyethyl)pyridin-2(1H)-ylidene]-hydrazono}ethyl)diazenyl] pyridinium chloride; 1-methyl-2-((E)-{(E)-[(2Z)-(1-methyl-pyridin-2(1H)-ylidene)hydrazono]methyl}diazenyl)-pyridinium chloride; 1-(2-hydroxyethyl)-2-[(E)-((E)-{(2E)-[1-(2-hydroxyethyl)pyridin-2(1H)-ylidene]hydrazono}methyl)diazenyl]-pyridinium acetate.

Among the additional natural direct dyes that may be used according to the invention, mention may be made of lawsone, juglone, alizarin, purpurin, carminic acid, kermesic acid, purpurogallin, protocatechaldehyde, indigo, isatin, curcumin, spinulosin and apigenidin. Use may also be made of extracts or decoctions comprising these natural dyes and especially henna-based poultices or extracts.

When they are present, the content of additional direct dyes in the composition generally ranges from 0.001% to 20% and preferably from 0.01% to 10% by weight relative to the weight of the composition.

The medium that is suitable for dyeing, also known as the dye support, generally comprises water or a mixture of water and of at least one organic solvent to dissolve the compounds that are not sufficiently water-soluble.

More particularly, the organic solvents are chosen from linear or branched and preferably saturated monoalcohols or diols, containing 2 to 10 carbon atoms, such as ethyl alcohol, isopropyl alcohol, hexylene glycol (2-methyl-2,4-pentanediol), neopentyl glycol and 3-methyl-1,5-pentanediol; aromatic alcohols such as benzyl alcohol and phenylethyl alcohol; glycols or glycol ethers, for instance ethylene glycol monomethyl, monoethyl and monobutyl ethers, propylene glycol or ethers thereof, for instance propylene glycol, butylene glycol or dipropylene glycol monomethyl ether; and also diethylene glycol alkyl ethers, especially of $C_1$-$C_4$, for instance diethylene glycol monoethyl ether or monobutyl ether, alone or as a mixture.

The common solvents described above, if they are present, usually represent from 1% to 40% by weight and more preferentially from 5% to 30% by weight relative to the total weight of the composition.

The dye composition that is useful in the context of the invention may also contain various adjuvants conventionally used in hair dye compositions, such as anionic, cationic, nonionic, amphoteric or zwitterionic surfactants or mixtures thereof, anionic, cationic, nonionic, amphoteric or zwitterionic polymers or mixtures thereof, mineral or organic thickeners, and in particular anionic, cationic, nonionic and amphoteric polymeric associative thickeners, antioxidants, penetrants, sequestrants, fragrances, buffers, dispersants, conditioning agents, for instance volatile or non-volatile, modified or unmodified silicones, film-forming agents, ceramides, preserving agents and opacifiers.

These above adjuvants are generally present in an amount, for each of them, of between 0.01% and 20% by weight relative to the weight of the composition.

Needless to say, a person skilled in the art will take care to select this or these optional additional compound(s) such that the advantageous properties intrinsically associated with the dye composition that is useful in the context of the invention are not, or are not substantially, adversely affected by the envisaged addition(s).

The pH of the dye composition that is useful in the context of the invention is generally between 3 and 12 approximately and preferably between 5 and 11 approximately. It may be adjusted to the desired value by means of acidifying or basifying agents usually used in the dyeing of keratin fibres, or alternatively using standard buffer systems. Modifying the pH within these ranges will promote the formation of compound (I) or (II).

Among the acidifying agents, examples that may be mentioned include mineral acids, for instance hydrochloric acid, nitric acid or sulfuric acid, or organic acids, for instance compounds comprising at least one carboxylic acid function such as acetic acid, tartaric acid, citric acid or lactic acid, a sulfonic acid function, a phosphonic acid function or a phosphoric acid function.

Among the basifying agents, examples that may be mentioned include aqueous ammonia, alkali metal carbonates, alkanolamines such as monoethanolamine, diethanolamine and triethanolamine, and also derivatives thereof, sodium hydroxide, potassium hydroxide and the compounds of formula (IV) below

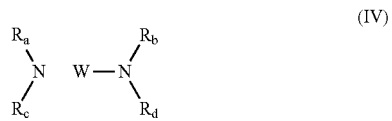

in which W is a propylene residue optionally substituted with a hydroxyl group or a $C_1$-$C_4$ alkyl radical; and Ra, Rb, Rc and Rd, which may be identical or different, represent a hydrogen atom or a $C_1$-$C_4$ alkyl or $C_1$-$C_4$ hydroxyalkyl radical.

The compounds of formula (I) may be obtained from the leuco compounds of formula (II) by reaction with atmospheric oxygen or via the action of an oxidizing agent, which may be any chemical oxidizing agent conventionally used in the field. Thus, it may be chosen from hydrogen peroxide, urea peroxide, alkali metal bromates, persalts such as perborates and persulfates, and also enzymes, among which mention may be made of peroxidases, 2-electron oxidoreductases such as uricases, and 4-electron oxygenases such as laccases. The oxidizing agent will preferably be hydrogen peroxide.

The oxidizing agent will also be necessary for obtaining simultaneous lightening of the keratin fibres (lightening dyeing) and/or when the composition contains oxidation bases or couplers.

The composition according to the invention will optionally comprise at least one such oxidizing agent.

In the case where the oxidizing agent(s) are present in the dye composition according to the invention, their amount will preferably range from 5% to 100% by weight and better still from 50% to 100% by weight relative to the total weight of the composition.

The dye composition that is useful in the context of the invention may be in various forms, such as in the form of liquids, creams or gels, or in any other form that is suitable for dyeing keratin fibres, and especially human hair.

The colouring obtained depends on the compounds that are applied to the keratin fibres. The colouring is more intense when all of these compounds are in the form of dyes of azomethine type bearing a pyrazolopyridine unit, i.e. when they are of formula (I). By promoting the formation of the compounds of formula (II) from the compounds of formula (I), the intensity of the colouring may be reduced until it disappears.

The dyeing process according to the invention comprises the application to the keratin fibres of at least one dye composition as defined above.

When an oxidizing agent is used, it may be present in the composition of the invention. It may also be applied separately, as a pretreatment or post-treatment.

The application of the composition of the invention may optionally be followed by rinsing.

The leave-on time for the dye composition is generally between 3 and 60 minutes, preferably between 5 and 40 minutes and even more preferentially between 10 and 30 minutes.

The application temperature generally used is room temperature, preferably between 25 and 55° C.

The examples which follow serve to illustrate the invention without, however, exhibiting a limiting nature.

EXAMPLES

Example 1: Synthesis of 2-[(3-{[4-imino-2,3,7-trimethyl-1,4-dihydro-5H-indol-5-ylidene]amino}pyrazolo[1,5-a]pyridin-2-yl)oxy]ethanol hydrochloride

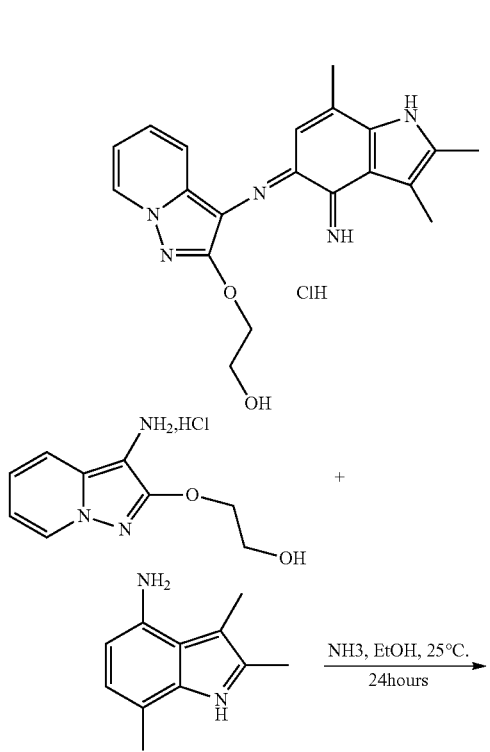

-continued

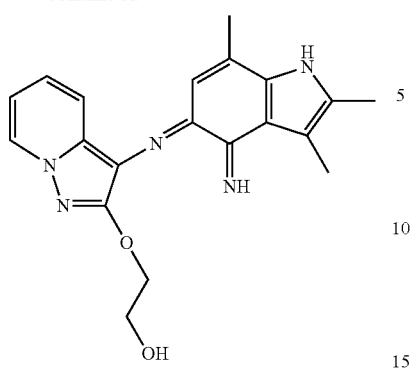

39.60 g (172.17 mmol) of 2-[(3-aminopyrazolo[1,5-a]pyridin-2-yl)oxy]ethanol hydrochloride are placed in a 2-liter one-necked round-bottomed flask equipped with a bubbler, and are dissolved in a mixture consisting of 80 ml of ethanol and 80 ml of water.

30 g (172.17 mmol) of 2,3,7-trimethyl-1H-indol-4-amine, 80 ml (860.85 mmol) of ammonia at 20% in water and 93 ml (860.85 mmol) of hydrogen peroxide at 30% in water are added to this solution.

The solution is then stirred at room temperature for 24 hours. The dark brown precipitate formed is isolated by filtration, washed with water and then dried in a desiccator under vacuum at 30° C. in the presence of a desiccant, to constant weight.

A product in the form of a dark brown powder is obtained.

The spectrometric analyses show that 2-[(3-{[4-imino-2,3,7-trimethyl-1,4-dihydro-5H-indol-5-ylidene]amino}pyrazolo[1,5-a]pyridin-2-yl)oxy]ethanol hydrochloride is obtained.

Example 2: Synthesis of 2-[(3-{[4-imino-7-methyl-1,4-dihydro-5H-indol-5-ylidene]amino}pyrazolo[1,5-a]pyridin-2-yl)oxy]ethanol

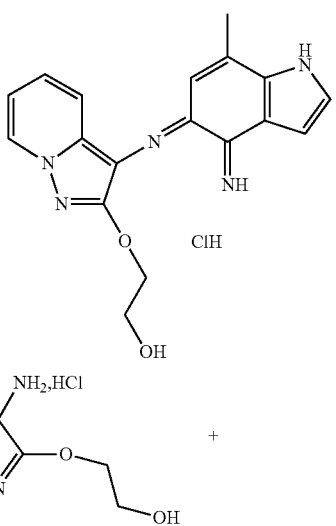

-continued

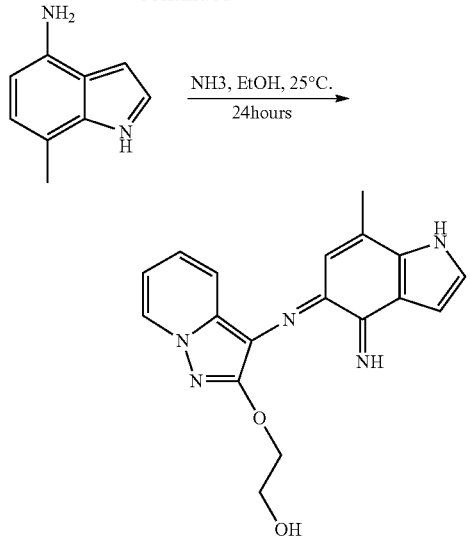

A mixture of 30 ml of water and 10 ml of ethanol is placed in a 250 ml one-necked round-bottomed flask equipped with a bubbler, followed by addition of 87.18 mg of 2-[(3-aminopyrazolo[1,5-a]pyridin-2-yl)oxy]ethanol hydrochloride and 55.5 mg of 7-methyl-1H-indol-4-amine.

4 ml of ammonia at 20% in water and 4 ml of 20-volumes aqueous hydrogen peroxide solution are added to this solution.

The solution is then stirred at room temperature for 24 hours. The dark precipitate formed is isolated by filtration, washed with water and then dried in a desiccator under vacuum at 30° C. in the presence of a desiccant, to constant weight.

A product in the form of a black powder is obtained.

The spectrometric analyses show that 2-[(3-{[4-imino-7-methyl-1,4-dihydro-5H-indol-5-ylidene]amino}pyrazolo[1,5-a]pyridin-2-yl)oxy]ethanol is obtained.

Example 3: Examples of Dyeing at Neutral pH

The following dye compositions were prepared using the ingredients indicated in the table below, and especially the dyes synthesized in Examples 1 and 2 above.

| | |
|---|---|
| Dye 1 or 2 [1] | $10^{-3}$ mol |
| pH 7 dye support | [2] |
| Demineralized water qs | 100 g |

[1] Dye synthesized in Example 1 or 2 above:

Dye 1
(synthesized in Example 1)

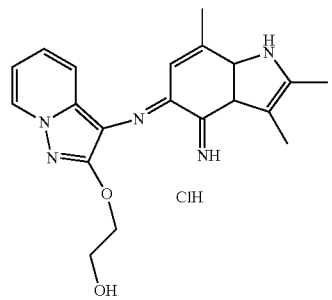 [SMILES: CC1=C/C(=N\c2c(OCCO)nn3ccccc23)C(=N)C2C(C)=C(C)NC12 ; Cl]

Dye 2
(synthesized in Example 2)

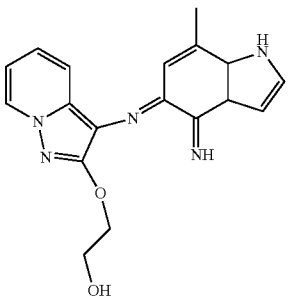 [SMILES: CC1=C/C(=N\c2c(OCCO)nn3ccccc23)C(=N)C2C=CNC12]

(2) pH 7 dye support

| | |
|---|---|
| 96° ethyl alcohol | 20.8 g |
| Pentasodium salt of diethylenetriaminepentaacetic acid as an aqueous solution at 40% by weight | 0.48 g AM* |
| ($C_8$-$C_{10}$alkyl) polyglucoside as an aqueous solution at 60% by weight | 3.6 g AM* |
| Benzyl alcohol | 2.0 g |
| Polyethylene glycol containing 8 units of ethylene oxide | 3.0 g |
| $Na_2HPO_4$ | 0.28 g |
| $KH_2PO_4$ | 0.46 g |

*AM: Active Material

Each composition was applied to locks of grey hair containing 90% white hairs. After a leave-on time of 30 minutes, the locks are rinsed, washed with a standard shampoo, rinsed again and then dried.

The shades obtained are given in the table below:

| | Dye | |
|---|---|---|
| | 1 | 2 |
| Shade observed | Brown | Dark brown |

For the colourings in the presence of an oxidizing agent: at the time of use, each of the compositions described above was mixed with an equal weight of 20-volumes aqueous hydrogen peroxide solution (6% by weight relative to the total weight of 100 grams). A final pH of 7 is obtained.

The shades obtained are given in the table below:

| | Dye | |
|---|---|---|
| | 1 | 2 |
| Shade observed | Brown | Dark brown |

Example 4: Examples of Dyeing in Basic Medium

The following dye compositions were prepared:

| | |
|---|---|
| Dye 1 or 2 | $10^{-3}$ mol |
| pH 9.5 dye support | (3) |
| Demineralized water qs | 100 g |

(3): pH 9.5 dye support

| | |
|---|---|
| 96° ethyl alcohol | 20.8 g |
| Pentasodium salt of diethylenetriaminepentaacetic acid as an aqueous 40% solution | 0.48 g AM* |
| $C_8$-$C_{10}$ alkyl polyglucoside as an aqueous solution at 60% by weight | 3.6 g AM* |
| Benzyl alcohol | 2.0 g |
| Polyethylene glycol containing 8 units of ethylene oxide | 3.0 g |
| $NH_4Cl$ | 4.32 g |
| Aqueous ammonia containing 20% $NH_3$ | 2.94 g |

*AM: Active Material

Each mixture obtained was applied to locks of grey hair containing 90% white hairs. After a leave-on time of 30 minutes, the locks are rinsed, washed with a standard shampoo, rinsed again and then dried.

The hair colouring is evaluated visually and/or measured.

The shades obtained are given in the table below:

| | Dye | |
|---|---|---|
| | 1 | 2 |
| Shade observed | Dark brown | Dark brown |

For colourings in the presence of an oxidizing agent: at the time of use, each of the compositions described above was mixed with an equal weight of 20-volumes aqueous hydrogen peroxide solution. A final pH of 9.5 is obtained.

For colourings in oxidizing medium: at the time of use, each of the compositions described above was mixed with an equal weight of 20-volumes aqueous hydrogen peroxide solution. A final pH of 9.5 is obtained.

The shades obtained are given in the table below:

| | Dye | |
|---|---|---|
| | 1 | 2 |
| Shade observed | Dark brown | Dark brown |

The colour of the locks was evaluated in the CIE L* a* b* system, using a Minolta Spectrophotometer CM2600D colorimeter (specular components included, illuminant D65, angle 10°).

In this L* a* b* system, the three parameters denote, respectively, L*: the colour intensity, a*: the green/red colour axis, and b*: the blue/yellow colour axis. For the intensity, the lower the value, the darker and more intense the colour.

The results are given in the table below:

| Dye | L* | a* | b* |
|---|---|---|---|
| 1 | 26.57 | 3.53 | 7.72 |

The invention claimed is:

1. A compound chosen from dyes of azomethine type bearing a pyrazolopyridine unit of formula (I), leuco forms of formula (II) thereof, optical isomers and geometrical isomers thereof, tautomers thereof, addition salts thereof with an acid or a base, and solvates or hydrates thereof:

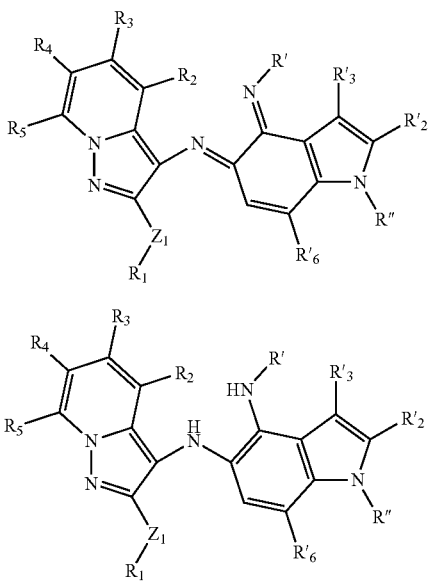

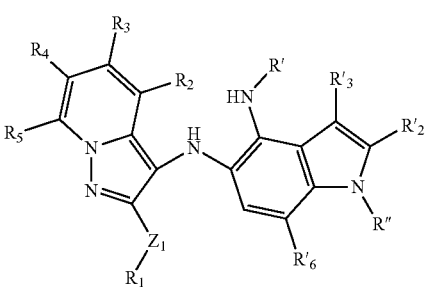

wherein in formulae (I) and (II), independently:
- $Z_1$ represents an oxygen atom or a group $—NR_6—$; and when $Z_1$ represents $—NR_6—$, then $R_1$ and $R_6$ may form, together with the nitrogen atom to which they are attached, an optionally substituted, 5- to 8-membered, saturated, unsaturated or aromatic heterocycle;
- $R_1$ and $R_6$ each independently represent:
  - a hydrogen atom;
  - a $C_1$-$C_{10}$ alkyl radical optionally interrupted with one or more non-adjacent heteroatoms, and/or optionally substituted, with one or more groups chosen from i) hydroxyl, ii) optionally substituted 5- to 8-membered, saturated, unsaturated or aromatic (hetero)cycle, iii) $—N(R')R''$, iv) $—N+R'R''R'''$ with $R'$, $R''$ and $R'''$ each independently representing a $C_1$-$C_6$ alkyl group; or
  - an optionally substituted, saturated, unsaturated or aromatic 5- to 8-membered (hetero)cycle;
- $R_2$, $R_3$, $R_4$ and $R_5$ each independently represent:
  - a hydrogen atom;
  - an optionally substituted $C_1$-$C_4$ alkyl radical; or
  - a group chosen from $—NH_2$, $—N(H)R_{10}$, $—N(R_{11})R_{12}$, $—OH$ and $—OR_9$, with $R_9$ and $R_{10}$ representing an optionally substituted, linear or branched $C_1$-$C_6$ alkyl, $R_{11}$ and $R_{12}$, which may be identical or different, representing an optionally substituted, linear or branched $C_1$-$C_6$ alkyl, it being optional for $R_{11}$ and $R_{12}$ to form, together with the nitrogen atom to which they are attached, a saturated, unsaturated or aromatic 5- to 8-membered heterocycle optionally containing one or more other heteroatoms or groups chosen from oxygen and nitrogen, the heterocycle being optionally substituted;
- $R_2$, $R_3$, $R_4$ and $R_5$ may form, in pairs, with adjacent radicals, an optionally substituted, saturated or unsaturated or aromatic (hetero)cycle;
- $R'_2$ and $R'_3$, which may be identical or different, represent:
  - a hydrogen atom;
  - a $C_1$-$C_6$ alkyl radical, optionally substituted with one or more hydroxyl radicals;
  - a $C_1$-$C_6$ alkyl carboxylate radical; or
  - a carboxyl radical;
- $R'$ represents:
  - a hydrogen atom;
  - a $C_1$-$C_6$ alkyl radical;
- $R'_6$ represents:
  - a hydrogen atom;
  - a halogen atom;
  - a linear or branched $C_1$-$C_{10}$ alkyl radical, optionally interrupted with one or more non-adjacent oxygen atoms and/or one or more non-adjacent divalent groups $—N(R'_9)—$ and optionally substituted with one or more radicals, which may be identical or different, chosen from $—OH$ and $—N(R'_7)R'_8$;
  - a carboxyl radical;
  - a $C_1$-$C_{10}$ alkyl carboxylate;
  - a radical $CONR'_7R'_8$;
  - a $C_1$-$C_{10}$ alkoxy radical or a $C_1$-$C_{10}$ (poly)hydroxyalkoxy radical;
  - a (poly)($C_1$-$C_{10}$ alkoxy)-($C_1$-$C_{10}$ alkoxy) radical; or
  - a radical $—O$-$Ak$-$N(R'_9)R'_{10}$ in which $Ak$ is a linear $C_1$-$C_8$ or branched $C_3$-$C_8$ divalent alkylene radical, optionally interrupted with one or more oxygen atoms and/or non-adjacent divalent groups $—N(R'_7)—$;
- $R'_7$ and $R'_8$, which may be identical or different, represent:
  - a hydrogen atom; or
  - a $C_1$-$C_8$ alkyl radical optionally substituted with one or more hydroxyl radicals;
- $R'_9$ and $R'_{10}$, which may be identical or different, represent i) a linear or branched $C_1$-$C_6$ alkyl radical, ii) a $C_2$-$C_6$ alkenyl radical or iii) a $C_2$-$C_6$ alkynyl radical;
- $R'_9$ and $R'_{10}$ may form, with the nitrogen that bears them, a saturated or unsaturated 5- to 8-membered heterocycle, one of the chain members optionally being an oxygen atom or a nitrogen atom, or a divalent radical $—N(R'_{11})—$ with $R'_{11}$ representing a hydrogen atom or a $C_1$-$C_4$ alkyl group, optionally substituted with one or more radicals chosen from $—OH$, $—N(R'_7)R'_8$ and $C_1$-$C_4$ alkyl;
- $R''$ represents:
  - a hydrogen atom; or
  - a linear or branched $C_1$-$C_{10}$ alkyl radical, optionally interrupted with an oxygen atom or a divalent group $—N(R)—$ with $R$ representing a hydrogen atom or a $C_1$-$C_4$ alkyl group;
wherein when the compound of formula (I) or (II) is positively charged, then it comprises as many anionic counterions as cationic charges to achieve the electrical neutrality of the molecule.

2. The compound according to claim 1, wherein $Z_1$ represents an oxygen atom or an $—N(H)—$ radical.

3. The compound according to claim 1, wherein $R_1$ represents a $C_1$-$C_6$ alkyl radical, a $C_1$-$C_6$ alkyl radical substituted with a hydroxyl group, a $C_1$-$C_6$ alkyl radical substituted with a (di)($C_1$-$C_4$ alkyl)amino, or a $C_1$-$C_6$ alkyl radical substituted with a nitrogenous heterocycle chosen from imidazolyl, pyrrolidinyl, piperidyl, morpholinyl and piperazinyl.

4. The compound according to claim 1, wherein $R_2$, $R_3$, $R_4$ and $R_5$ independently represent a hydrogen atom or a $C_1$-$C_4$ alkyl radical.

5. The compound according to claim 1, wherein $R'_2$ and $R'_3$ independently represent a hydrogen atom or a $C_1$-$C_4$ alkyl radical optionally substituted with one or more hydroxyl radicals.

6. The compound according to claim 1, wherein $R'$ represents a hydrogen atom or a $C_1$-$C_4$ alkyl radical.

7. The compound according to claim 1, wherein $R'_6$ represents i) a hydrogen atom; ii) a linear or branched $C_1$-$C_6$ alkyl radical, optionally substituted with a hydroxyl radical; iii) a $C_1$-$C_6$ hydroxyalkoxy radical; or iv) a radical —O-Ak-$NR'_9R'_{10}$ in which Ak denotes a linear divalent $C_1$-$C_8$ alkylene radical with:

$R'_9$ and $R'_{10}$ independently denoting a saturated, linear or branched $C_1$-$C_4$ alkyl radical; or alternatively $R'_9$ and $R'_{10}$ form, together with the nitrogen atom that bears them, a heterocycle chosen from pyrrolidinyl, morpholinyl, imidazolyl, piperazinyl and piperidyl, said heterocycle being optionally substituted with one or more radicals chosen from —OH and $C_1$-$C_4$ alkyl.

8. The compound according to claim 1, wherein R" represents a hydrogen atom or a linear $C_1$-$C_6$ alkyl radical.

9. The compound according to claim 1, chosen from the compounds of formulae (I) and (II), and also the optical isomer, geometrical isomer and tautomer forms thereof, the addition salts thereof with an acid or a base, and the solvates or hydrates thereof:

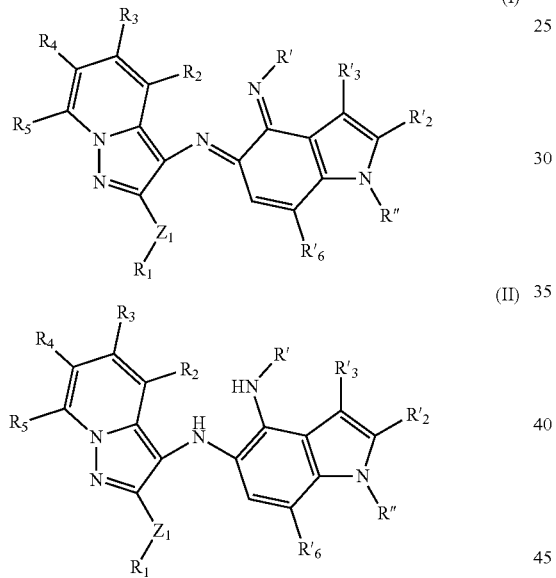

wherein in formulae (I) and (II):
$R_1$=—$CH_2CH_2OH$, —$CH_2CH_2N(CH_3)_2$, —$CH_2CH_2CH_2N(CH_3)_2$ when $Z_1$=O,
$R_1$=—$CH_2CH_2N(CH_3)_2$, —$CH_2CH_2CH_2N(CH_3)_2$ when $Z_1$=—$N(R_6)$— and $R_6$ represents a hydrogen atom,
R', $R_2$, $R_3$, $R_4$ and $R_5$ denote a hydrogen atom,
$R'_2$, $R'_3$ and R", which may be identical or different, denote a hydrogen atom or a methyl radical, and
$R'_6$ denotes a hydrogen atom or a methyl, ethyl, —O—$(CH_2)_2$—OH, —O—$(CH_2)_3$—OH, —O—$(CH_2)_2$-Het or —O—$(CH_2)_3$-Het radical with Het representing a pyrrolidinyl or morpholino or imidazolyl or N-methylpiperazino or piperidino group.

10. A composition for dyeing keratin fibers comprising, in a medium that is suitable for dyeing, at least one compound as defined in claim 1.

11. The composition according to claim 10, wherein the compound are present in an amount ranging from 0.01% to 15% by weight relative to the total weight of the composition.

12. The composition according to claim 10, wherein it also comprises one or more oxidizing agents.

13. A process for dyeing keratin fibers, wherein a composition according to claim 10 is applied to the keratin fibers.

14. A process for preparing compounds of formulae (I) or (II) as defined in claim 1, according to the following scheme:

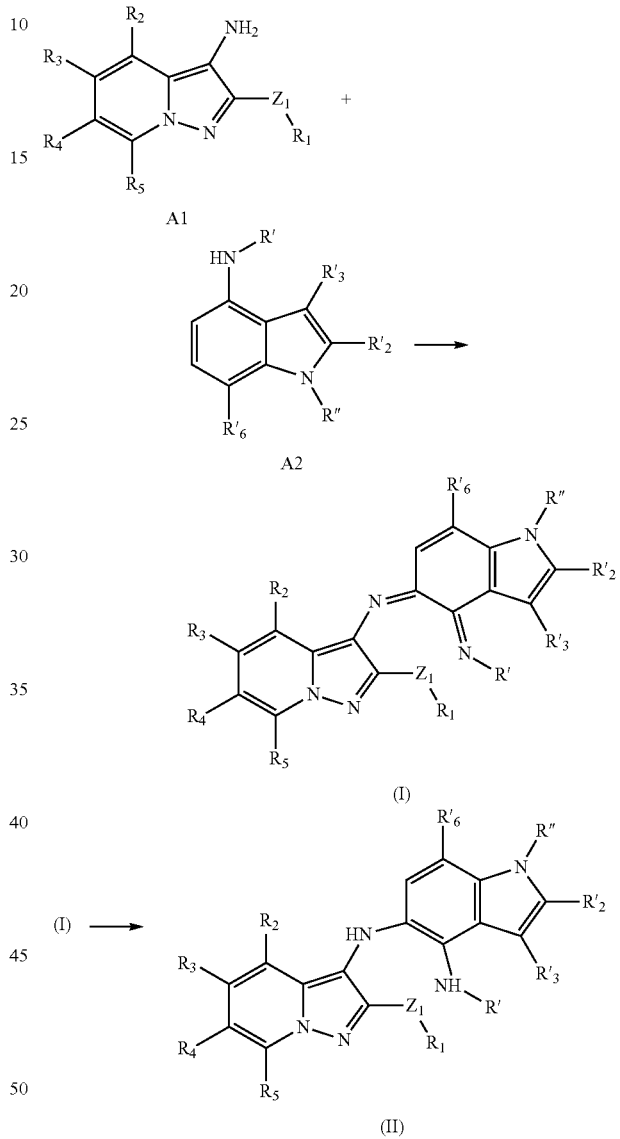

comprising:
in a first stage, in reacting a pyrazolo[1,5-a]pyridine compound A1 comprising an amino group in position 3 with an indole compound A2 which is free in position 5 and comprising in position 4 an amino group,
wherein this reaction is optionally performed i) in a polar protic solvent or a mixture of water/$C_1$-$C_{10}$ alcohol ii) and/or in the presence of one or more basifying agents, chosen from sodium hydroxide, potassium hydroxide, and/or a mineral carbonate iii) and/or in the presence of a chemical oxidizing agent iv) and/or at a temperature between room temperature, i.e. 25° C., and the reflux temperature of the solvent, and in a second stage, in maintaining the reaction medium under stirring for a time ranging from 5 minutes and 48 hours;

wherein the reaction product (I) is then optionally purified;

and further optionally wherein when compound (I) is then purified, compound (I) once purified is reduced using a reducing agent, or using transition metals or alternatively by reduction with hydrides or borohydrides, or with thioglycolic acid derivatives, to give the leuco compound (II); optionally followed by a step of purification via a standard technique to give the leuco compound (II);

and further optionally wherein when compound (I) is not then purified, compound (I) is reduced using a reducing agent as mentioned previously to give the leuco compound (II), optionally followed by a step of purification.

* * * * *